(12) United States Patent
Cates et al.

(10) Patent No.: US 7,951,849 B2
(45) Date of Patent: May 31, 2011

(54) FLUID-BICONTINUOS PARTICLE-STABILISED GELS

(75) Inventors: Michael Elmhirst Cates, Edinburgh (GB); Paul Stephen Clegg, Edinburgh (GB); Stefan Ulrich Egelhaaf, Duesseldorf (DE); Wilson Che Poon, Edinburgh (GB)

(73) Assignee: The University Court of the University of Edinburgh, Ediaburgh (GB)

( * ) Notice: Subject to any disclaimer, the term of this patent is extended or adjusted under 35 U.S.C. 154(b) by 771 days.

(21) Appl. No.: 11/630,084

(22) PCT Filed: Jul. 1, 2005

(86) PCT No.: PCT/GB2005/002577
§ 371 (c)(1),
(2), (4) Date: Jan. 24, 2008

(87) PCT Pub. No.: WO2006/003403
PCT Pub. Date: Jan. 12, 2006

(65) Prior Publication Data
US 2008/0125500 A1 May 29, 2008

(30) Foreign Application Priority Data

Jul. 2, 2004 (GB) .................................. 0414829.2
Aug. 3, 2004 (GB) .................................. 0417437.1

(51) Int. Cl.
*C09K 3/00* (2006.01)
(52) U.S. Cl. .......................................... 516/99; 516/111
(58) Field of Classification Search ..................... 516/99, 516/111
See application file for complete search history.

(56) References Cited

U.S. PATENT DOCUMENTS 6,638,885 B1 * 10/2003 McGrath et al. ................ 501/80
2003/0183804 A1 10/2003 Martin et al.

FOREIGN PATENT DOCUMENTS

EP 0 309 054 A 3/1989
EP 0 478 326 A 4/1992

OTHER PUBLICATIONS

Aveyard et al. (Emulsions stabilized solely by colloidal particles, Advances in Colloid and Interface Science, 100-102 (2003) 503-546).*
The International Search Report dated Oct. 21, 2005.
Kunieda, et al: "Spontaneous Formation of Highly Concentrated Water-in-Oil Emulsions (Gel-emulsions)"; Langmuir, vol. 12, May 1, 1996, pp. 2136-2140.
Tauer, et al: "Polymer Dispersions as Intermediate State During the Synthesis of Specialty Polymers"; Macromolecular Symposia, Wiley Vch Verlag, Weinheim, DE, No. 179, 2002, pp. 27-52.
Gan, et al: "Microporous polymeric composites from bicontinuous microemulsion polymerization using a polymerizable nonionic surfactant"; Polymer, Elsevier Science Publishers B. V., GB, vol. 38, No. 21, Oct. 1997, pp. 5339-5345.
T, et al: "Porous polymeric membranes by bicontinuous microemulsion polymerization: effect of anionic and cationic surfactants"; Polymer, Elsevier Science Publishers B. V., GB, vol. 37, No. 26, 1996, pp. 5917-5925.
Casagrande, et al: ">: Realization et premieres observations des proprietes interfaciales janus beads: Realization and First Observation of Interfacial Properties"; Comptes Rendus Des Seances De L'Academie Des Sciences. Serie II :Mechanique, Physique, Chimie, Sciences De La Terre, Sciences De L'Univers, Gauthier-Villars. Montreuil, FR, vol. 306, No. Serie II. 1998, pp. 1423-1425.

* cited by examiner

*Primary Examiner* — Ling-Siu Choi
*Assistant Examiner* — Chun-Cheng Wang
(74) *Attorney, Agent, or Firm* — Edwards Angell Palmer & Dodge LLP; Scott D. Wofsy; George N. Chaclas

(57) ABSTRACT

The present invention relates to the field of gels. The invention also relates to an improved method for manufacturing gels. In particular the invention relates to a new class of material, fluid-bicontinuous particle-stabilized gels, and a method of making the same. The fluid-bicontinuous particle-stabilized gels comprise at least a first fluid, a second fluid, and a continuous layer of particles positioned at a continuous interface between the first fluid and the second fluid.

37 Claims, 5 Drawing Sheets

FLUID-BICONTINUOS PARTICLE-STABILISED GELS

CROSS-REFERENCE TO RELATED APPLICATION

This application is the U.S. national phase, pursuant to 35 U.S.C. §371, of international application No. PCT/GB2005/002577, published in English on Jan. 12, 2006 as international publication No. WO 2006/003403 A1, which claims the benefit of British application Ser. No. GB 0414829.2, filed Jul. 2, 2004 and British application Ser. No. GB 0417437.1, filed Aug. 3, 2004, the disclosure of which applications are incorporated herein in their entireties by this reference.

BACKGROUND OF THE INVENTION

The present invention relates to the field of gels. The invention also relates to an improved method for manufacturing gels.

Gels are versatile soft solids (that is, materials that are between solids and liquids) with useful properties. They are used in many products in a wide range of applications, for example; personal care, foodstuffs, drilling muds and pharmacological uses. Many of these properties exploit the presence of a finite elastic modulus, accompanied by yield behaviour enabling flow under large stresses. Various routes to the creation of gels exist, but since the variety of product behaviours required is almost limitless, any new generic technology for gel creation opens wide possibilities for new and improved products.

Some gels consist of equilibrium structures in a given range of temperatures for a given state of chemical bonding. However, other gels are non-equilibrium arrested states whose properties depend on process history. The properties of non-equilibrium gels can be tuned during formulation and manufacture, making them useful in product design.

Fluid-bicontinuous gels are known to the art. In this context, "fluid-bicontinuous" denotes that at any instant, two continuous inter-penetrating domains, each containing a different fluid, are present throughout a gel. Particle-stabilised materials, including particle-stabilized gels, are also known to the art. The two fluids are inter-meshed such that the surfaces of the fluids are in contact with each other. However, both these gels and materials have limitations and shortcomings which restrict the extent to which their physical and chemical properties can be controlled to meet desired criteria.

Also, fluid-bicontinuous gels have different physical properties from gels that comprise discrete droplets. For example, discrete droplets form a fluid phase at low density but transform into gels under compression by either external or internal (bonding) forces; this allows gels to be created from traditional emulsions stabilized by surfactant molecules. The differences in physical properties can also include enhanced stability under gravity and/or under exposure to solvents. In particular, droplet emulsion gels may dissolve if exposed to an excess of their continuous phase. Moreover, the property of fluid bicontinuity is itself desirable in certain applications, such as a gel through which hydrophobic and hydrophilic molecules are both freely permeable. However, as will become apparent from the discussion of the prior art below, known fluid-bicontinuous gels are generally equilibrium structures that cease to be stable upon temperature change and/or exposure to external solvents.

Fluid-bicontinuous states of two solvents can be created temporarily. These temporary states may be established in several ways. One such method is to apply a high level of agitation to a system where two solvents have roughly equal volume fraction and viscosity. Another is to raise the temperature of a mixture of two immiscible solvents until the fluids become miscible, allow them to mix microscopically, and then quench the mixture to below the critical temperature, at which point the fluids become immiscible, so that spinodal decomposition (transition from a single phase into two separate phases) occurs. This is well known to give bicontinuous structures (for solvents of similar viscosity), when the fluid: fluid composition ratio is in the range 30:70 to 70:30, with the most robust examples being around 50:50. However, without stabilisation of some sort, such bicontinuous states are transient.

Fluid-bicontinuity can be temporarily sustained in a system where one or more solvent is a high molecular weight polymer of high viscosity. However, to trap the structure it is necessary to pass below the glass transition temperature of the relevant polymer so that it becomes a solid phase. As such, the resulting structure is no longer fluid-bicontinuous. Impermanent fluid-bicontinuous systems of this type are temporarily sustainable and only at restricted temperatures. Also, they may be denatured by the presence of external solvents.

A fluid-bicontinuous state can also be obtained by the addition of a surfactant which absorbs onto the interface between two fluids. The bicontinuous state is itself generally highly fluid, thermodynamically stable and the resultant material is commonly called a bicontinuous microemulsion. This is not a gel. Fluid-bicontinuous gels can however be obtained at high enough surfactant concentration, in the form of bicontinuous (cubic) liquid crystals. These are thermodynamic phases, stable within a modest temperature range only. Their pore-size and elastic properties can only be varied within a very limited range.

Surfactants and their mixtures are also widely used to stabilise ordinary emulsions (as opposed to microemulsions), which are thermodynamically metastable. Such metastable emulsions are generally not bicontinuous but are a dispersion of spheres of one fluid in the other. These emulsions remain liquid unless the dispersed phase has a high volume fraction, in which case a biliquid foam, which is a type of gel, is produced. However, such gels comprise discrete emulsion droplets and therefore are not fluid-bicontinuous. In addition, biliquid foam gels are stabilised by non-rigid surfactant monolayers, and thus are not particle-stabilised. Furthermore, they can be denatured by coming into contact with external solvents.

Certain structures, often called Pickering emulsions, utilise near-neutral wetting (NNW) particles to stabilise discrete, usually spherical emulsion droplets. In this context, near-neutral wetting particles are particles that span the interface between two immiscible fluids, such that the angle at the fluid-fluid-solid contact line is not too far from 90 degrees. NNW particles are a subset of partially wetting (PW) particles—particles that have a contact angle that is strictly greater than 0 degrees and less than 180 degrees. The angle 90 degrees is known as the neutral wetting (NW) angle. The NW angle of 90 degrees is included when referring to NNW particles, the NNW angle and PW particles. NNW particles are known to have a strong affinity to the interface between fluids. Once contacted by such an interface they are attached almost irreversibly. In particular the timescale for such particles to become detached from the interface by Brownian motion is extremely large. As Pickering emulsions are comprised of discrete emulsion droplets, stabilised by NNW particles, they are not fluid-bicontinuous, nor usually are they gels.

However, if the particle coverage on the fluid-fluid interfaces within a Pickering emulsion is sufficient, these interfaces are known to become locally rigid, even if the interaction between the colloidal particles is repulsive. This is because these particles are jammed together by the tendency of a fluid-fluid interface to reduce its area. Such rigidity does not in general impart macroscopic rigidity to the sample, because a suspension of droplets with rigid surfaces is not in general rigid. Note that a rigid interface can be considered as an interface substantially covered in particles, the particles being forced into intimate contact such that they have restricted movement, thereby imparting a substantial amount of inflexibility to the interface.

Gels formed by compression of Pickering emulsion droplets are known, which again are stabilised by particles but are not fluid-bicontinuous (see EP 0309054, U.S. Pat. No. 2,968,066 and Materials based on solid-stabilized emulsions, F. Leal-Calderon et al., *Journal of Colloid and Interfacial Science*, 275, 2004, 659). These stabilised compositions become macroscopically rigid only when the droplets are pressed into contact. That is, they generally require an external force acting on them in order to establish macroscopic rigidity (although in some cases the drainage force of gravity, or internal attractions among the droplets, will suffice). Particle-stabilised gels created by compression of Pickering emulsions generally comprise droplets, and are not fluid-bicontinuous. Furthermore, they can be denatured by coming into contact with external solvents. In particular, they can be dissolved in a solvent comprising the same fluid as the continuous fluid phase of the emulsion, or another fluid miscible with that fluid.

In summary therefore, the prior art materials referred to above have significant limitations in terms of their properties, their function and their tunability. Some prior art materials provide temporary macroscopically rigid structures, but these are influenced by external forces (or the lack thereof), such as drainage under gravity. Most of the prior art materials are affected by the presence of external solvents. Many of the materials exist as thermodynamic equilibrium states and therefore cannot be tuned during processing, and cannot be maintained as gels outside the narrow range of thermodynamic conditions for which they are in the equilibrium state. Others have only short-lived existence.

SUMMARY

It is amongst the objects of the embodiments of the invention to obviate or at least mitigate some of the drawbacks associated with the prior art.

Further aims and objects of the invention will become apparent from a reading of the following description.

According to a first aspect of the present invention there is provided a fluid-bicontinuous particle-stabilised gel comprising:
a first fluid and a second fluid which are immiscible within a specific temperature range; and
a stabilising particle layer comprising a continuous layer of stable particles in intimate contact, the particles positioned at a continuous interface between the first fluid and second fluids and wherein the first and second fluid are interpenetrating domains.

The stabilising particle layer is, in effect, a substantially rigid layer of colloidal particles that are held, of forced, together. The particles are not dispersed by the application of external forces (that is, forces external of the gel), unless specifically designed to do so under specific conditions, as they are held together by attractive forces, and/or are forced together by the interfacial tension between the two fluids. This forces the interfacial particles into intimate contact so that they are jammed together in an arrested state, therefore creating a solid film of particles. The situating of these particles on the interface therefore has a stabilising effect which confers useful properties such as macroscopic rigidity and fluid bicontinuity. The macroscopic rigidity allows fluid-bicontinuous particle-stabilised gels to maintain their structure under the forces of gravity, and to support relatively heavy objects indefinitely against the force of gravity. In addition, the fluid bicontinuity allows fluid-bicontinuous particle-stabilised gels to remain robust against attack by external solvents.

Preferably the first fluid is hydrophobic and the second fluid is hydrophilic, or vice versa.

Optionally one of the fluids is an oil.

Preferably one of the fluids is water.

Optionally one of the fluids is an alcohol.

Optionally the fluid-bicontinuous particle-stabilised gel comprises a strongly fluid asymmetric fluid-bicontinuous state.

This allows a situation where one fluid is in excess of the other, which typically makes bicontinuity very difficult. In this case it is possible due to the use of particles which deviate from neutral wetting conditions.

Preferably the continuous layer of particles comprises partially wetting (PW).

Preferably the PW particles comprise near-neutral wetting (NNW) particles.

NNW particles are most effective because they are closest to the neutral wetting (NW) condition (where the fluid-fluid-solid contact angle is close to 90 degrees). NNW particles sit centrally on the interface between the two fluids.

Preferably the NNW particles have a contact angle between 70 and 110 degrees.

More preferably the NNW particles have a contact angle between 75 and 105 degrees.

It has been found that a wetting angle within this range confers adequate stability to the fluid-bicontinuous fluid-stabilised gels.

Still more preferably the NNW particles have a contact angle between 85 and 95 degrees.

The best stabilising effect is found in this range, as it is closest to the neutral wetting angle of 90 degrees.

Preferably the PW particles are in an arrested state.

In the arrested state the particles are in intimate contact at the interface between the two fluids such that they form a substantially rigid solid film. In the arrested state, the particles have restricted mobility, and are substantially stationary.

Optionally the PW particles are magnetically active.

It is this property which allows a relatively simple reverse fluidization of the gel as a magnetic field can be used to effectively force the particles off the interface between the two fluids such that the interpenetrating domains are no longer in an arrested state.

A preferable option is that the magnetically active PW particles are superparamagnetic.

Superparamagnetic materials are magnetic only in a magnetic field and they lose all residual magnetism when the magnetic field is removed.

Alternatively the PW particles are electrically conductive.

Preferably the PW particles are silica beads.

Optionally the PW particles are Janus beads.

A Janus bead is a substantially spherical colloidal particle with hydrophilic and hydrophobic hemispheres, separated by a sharply defined equator.

Optionally the PW particles are globular biomolecules.

Optionally the PW particles are colloidal particles with mixed polymer surfaces comprising flexible chains of two types, A and B, spread across the PW particle surface; wherein A and B are chosen so that A has an affinity for the first fluid, and B has an affinity for the second fluid, or vice versa.

Optionally the PW particles are spherical micelles, comprising an equal mixture of XZ and YZ block copolymers wherein X has an affinity for the first fluid, and Y has an affinity for the second fluid, or vice versa, and with Z insoluble in both the first and the second fluids.

Optionally the PW particles are colloidal particles with micro-heterogeneous wetting properties at different patches on their surfaces.

Preferably spontaneous curvature is imposed by manipulating the PW particles sequestered at the interface such that the fluid-fluid-solid contact angle is deliberately deviated from 90 degrees.

Spontaneous curvature can be used to counterbalance the tendency of bicontinuous states to curve towards the minority phase, which can result in the loss of bicontinuity.

Optionally the fluid-bicontinuous particle-stabilised gel structure comprises a fully ordered, three-dimensional periodic domain.

A fully ordered, three-dimensional periodic domain is a repeating three-dimensional structure, with regular dimensions, a fixed structure and a defined shape.

Optionally the fluid-bicontinuous particle-stabilised gel structure comprises an amorphous arrangement of the two interpenetrating domains.

An amorphous arrangement of two interpenetrating domains is an irregular three-dimensional structure where the two domains do not have a fixed structure or defined shape.

Optionally further particles, structurants or additives are present in one or both of the first and second fluids.

Optionally the fluid-bicontinuous particle-stabilised gel further comprises particles with attractive interactions.

Optionally the fluid-bicontinuous particle-stabilised gel comprises particles in a fluid or aggregated state, within one or both of the first and second fluids.

Optionally the fluid-bicontinuous particle-stabilised gel further comprises emulsion droplets, in a fluid or aggregated state, within one or both of the first and second fluids.

Optionally the fluid-bicontinuous particle-stabilised gel comprises a plurality of interpenetrating domains, which comprise a multicontinuous fluid or gel structure; the fluid-bicontinuous particle-stabilised gel being simultaneously permeable to a plurality of mutually immiscible fluids.

The fluid-bicontinuous particle-stabilised gel contains two immiscible fluids that form two separate domains. These separate domains are permeable to fluids with different properties. Therefore, the fluid-bicontinuous particle-stabilised gels can transport different types of fluid simultaneously.

Preferably the fluid-bicontinuous particle-stabilised gel is insoluble in water and oil based solvents but remains permeable to both oil and water based solvents.

This means that the fluid-bicontinuous particle-stabilised gel can withstand a variety of conditions without degrading. Also, it allows the fluid-bicontinuous particle-stabilised gel to act as a medium for oil and water based solvents without degrading.

Optionally the fluid-bicontinuous particle-stabilised gel comprises a first fluid and a second fluid of different refractive index, wherein the first fluid has a refractive index lower than the second fluid, or vice versa.

Optionally the fluid-bicontinuous particle-stabilised gel displays thermal conductivity, adjustable by formulation.

Optionally the fluid-bicontinuous particle-stabilised gel is adapted to transform to a substantially fluidised state.

Preferably the fluidization is reversible.

Optionally the fluid-bicontinuous particle-stabilised gel in the reversibly fluidisable state comprises an initial arrested state and a final re-arrested state that the fluid-bicontinuous particle-stabilised gel reverts to.

Optionally the fluid-bicontinuous particle-stabilised gel in the reversibly fluidisable state is macroscopically pliable.

A macroscopically pliable material can be easily bent or moulded and is substantially flexible. This is in contrast to a macroscopically rigid material.

Optionally the fluid-bicontinuous particle-stabilised gel in the reversibly fluidisable state comprises an initial arrested state, and a final re-arrested state, that have different morphologies.

Optionally the re-arrested state comprises droplets, parallel flat layers or cylinders, whose properties on re-arrest are different from the initial state.

According to a second aspect of the present invention there is provided a method of altering the properties of a fluid-bicontinuous particle-stabilised gel of the first aspect using magnetism.

The method of altering the properties of a fluid-bicontinuous particle-stabilised gel using magnetism comprises the steps of;
    subjecting the fluid-bicontinuous particle-stabilised gel to a magnetic field, and
    removing the particles from the interface using the magnetic field,
wherein the initial fluid-bicontinuous particle-stabilised gel is subsequently rendered entirely fluid by removal of the particles from the interface.

According to a third aspect of the present invention there is provided a method of making a gel, the method comprising the steps of:
    providing PW particles into approximately equal volumes of at least two fluids, at a temperature where the fluids are miscible,
    changing the temperature to one at which the fluids are immiscible, to cause phase separation of the fluids, thereby forming a gel having interpenetrating fluid domains with the PW particles positioned at a continuous interface between the fluids.

Preferably the phase separation is spinodal decomposition.

According to a fourth aspect of the present invention there is provided a method of making a fluid-bicontinuous particle-stabilised gel, comprising the steps of:
    dispersing PW particles in a mixture of two solvents by means of mixing, thereby creating a bicontinuous state with more interfacial area than is required to accommodate all of the PW particles,
    stopping the mixing so that the PW particles come into intimate contact on a continuous fluid-fluid interface, precipitating gel formation.

According to a fifth aspect of the present invention there is provided a method of making a Janus bead, comprising the steps of:
    mixing together approximately equal quantities of spherical micelles comprising XZ and YZ block copolymers, wherein X, Y and Z are polymer chains, in a solution comprising approximately equal volumes of at least two fluids, at a temperature range where the fluids become miscible, and under such conditions that mixed micelles form spontaneously;

subsequently altering the temperature to a temperature in the temperature range where the fluids are immiscible, causing spinodal decomposition to form a two-phase region and thereby sequestering the block copolymers at an interface between the fluids;

maintaining a temperature such that the Z polymer chains remain above their glass transition temperature and the XZ and YZ block copolymers migrate to opposite sides of the micelle;

altering the temperature such that the Z polymer chains pass through their glass transition temperature and the segregated micelle block copolymers are made stable, thus creating particles with hemispheres of opposite wetting properties.

According to a sixth aspect of the present invention there is provided a method of making a Janus bead, comprising the steps of;

preparing a fluid-bicontinuous particle-stabilised gel;

coating substantially one half of the particles in the fluid-bicontinuous particle-stabilised gel with substances that are dissolved in one or both of the first fluids and the second fluids.

According to the seventh aspect of the present invention there is provided a fluid-bicontinuous particle-stabilised gel comprising;
a first fluid
a second fluid, and
a continuous layer of particles
wherein the first fluid and the second fluid are immiscible within a specific temperature range, and wherein the continuous layer of particles comprises a rigid film, positioned at a continuous interface between the first fluid and the second fluid.

Optionally further particles are suspended in one or both of the first and second fluids.

Optionally further structurants or additives are present in one or both of the first and second fluids.

Preferably the first fluid is hydrophobic and the second fluid is hydrophilic, or vice versa.

Optionally one of the fluids is an oil.

Preferably the oil is an aliphatic hydrocarbon.

Still more preferably the oil is dodecane.

Preferably one of the fluids is water.

Optionally one of the fluids is an alcohol.

Preferably the alcohol is ethanol.

Preferably the continuous layer of particles comprises partially wetting (PW) particles, which have a fluid-fluid-solid contact angle of 0 to 180 degrees.

Preferably the PW particles comprise near-neutral wetting (NNW) particles.

Optionally the NNM particles have a contact angle between 60 and 120 degrees.

Preferably the NNW particles have a contact angle between 70 and 110 degrees.

More preferably the NNW particles have a contact angle between 85 and 95 degrees.

Preferably the NNW particles are in an arrested state.

Preferably the NNW particles are silica beads.

Optionally the NNW particles are Janus beads.

Optionally the NNW particles are colloidal particles with mixed polymer surfaces comprising flexible chains of two types, A and B, spread across the NNW particle surface; wherein A and B are chosen so that A has an affinity for the first fluid, and B has an affinity for the second fluid, or vice versa.

Preferably the flexible chains are spread substantially uniformly over the NNW particle surface.

Preferably the flexible chains are grafted to the NNW particle surface at one end.

Optionally the NNW particles are spherical micelles, comprising an equal mixture of XZ and YZ block copolymers wherein X has an affinity for the first fluid, and Y has an affinity for the second fluid, or vice versa, and with Z insoluble in both the first and the second fluids.

Optionally the NNW particles are colloidal particles with micro-heterogeneous wetting properties at different patches on their surfaces.

Optionally the NNW particles are globular biomolecules.

Preferably the NNW particles are globular proteins.

Optionally the fluid-bicontinuous particle-stabilised gel comprises a strongly fluid asymmetric fluid-bicontinuous state.

Optionally a spontaneous curvature is imposed on the interface between the first and the second fluid.

Preferably, the spontaneous curvature is imposed by manipulating the NNW particles sequestered at the interface such that the fluid-fluid-solid contact angle is deliberately deviated from 90 degrees.

Optionally the fluid-bicontinuous particle-stabilised gel structure comprises a fully ordered, three-dimensional periodic domain.

Optionally the fluid-bicontinuous particle-stabilised gel structure comprises an amorphous arrangement of the two interpenetrating domains.

Optionally the fluid-bicontinuous particle-stabilised gel comprises colloidal particles with attractive interactions.

Optionally the fluid-bicontinuous particle-stabilised gel comprises colloidal particles, in a fluid or aggregated state, within one or both of the first and second fluids.

Optionally the fluid-bicontinuous particle-stabilised gel comprises emulsion droplets, in a fluid or aggregated state, within one or both of the first and second fluids.

Optionally the fluid-bicontinuous particle-stabilised gel comprises a plurality of interpenetrating domains, which comprise a multicontinuous fluid or gel structure; wherein the fluid-bicontinuous particle-stabilised gel is simultaneously permeable to a plurality of mutually immiscible fluids.

Optionally the multicontinuous fluid or gel structure comprises fluid-bicontinuous particle-stabilised gels.

Preferably the fluid-bicontinuous particle-stabilised gel is insoluble in water and oil based solvents but remains permeable to both oil and water based solvents.

Preferably the fluid-bicontinuous particle-stabilised gel has a yield stress that is adjustable by formulation.

Preferably the fluid-bicontinuous particle-stabilised gel has a shear modulus that is adjustable by formulation.

Optionally the fluid-bicontinuous particle-stabilised gel comprises fluid domains with a characteristic length scale, defining the pore size, that is adjustable by formulation.

Optionally the fluid-bicontinuous particle-stabilised gel comprises a first fluid and a second fluid of different refractive index, wherein the first fluid has a refractive index lower than the second fluid, or vice versa.

Preferably the first fluid and the second fluid of different refractive index have a ratio of refractive indices greater than 2.

More preferably the first fluid and the second fluid of different refractive index have a ratio of refractive indices greater than 2.5.

Preferably the fluid-bicontinuous particle-stabilized gel has optical properties that are adjustable by formulation.

Optionally the fluid-bicontinuous particle-stabilised gel displays thermal conductivity, adjustable by formulation.

Optionally the NNW particles have magnetic properties.

Optionally the NNW particles have electrical conductivity.

Optionally the fluid-bicontinuous particle-stabilised gel is able to make a transition to a substantially fluidised state, wherein the fluidization is reversible.

Optionally the fluid-bicontinuous particle-stabilised gel in the reversibly fluidisable state comprises an initial arrested state and a final re-arrested state that the fluid-bicontinuous particle-stabilised gel reverts to.

Optionally the fluid-bicontinuous particle-stabilised gel in the reversibly fluidisable state is macroscopically pliable.

Preferably the fluid-bicontinuous particle-stabilised gel in the reversibly fluidised state comprises a mobilized particle layer at the continuous interface between the first fluid and the second fluid.

Optionally the fluid-bicontinuous particle-stabilised gel in the reversibly fluidisable state comprises an initial arrested state, and a final re-arrested state, that are anisotropic.

Optionally the re-arrested state ceases to be a fluid-bicontinuous particle-stabilised gel.

Optionally the re-arrested state comprises droplets, parallel flat layers or cylinders, whose properties on re-arrest are different from the initial state.

According to a eighth aspect of the present invention there is provided a generic method of making a gel, comprising the steps of;
dissolving NNW particles in a solution comprising approximately equal volumes of at least two solvents, immiscible at a defined temperature range, at a second temperature range where the two solvents become miscible,
changing the temperature to a two-phase region where the solvents are immiscible, causing phase separation, thereby sequestering the NNW particles at an interface between the solvents.

Preferably the phase separation is spinodal decomposition.

According to a ninth aspect of the present invention there is provided a generic method of making a fluid-bicontinuous particle-stabilised gel, comprising the steps of;
dispersing NNW particles in a mixture of two solvents by means of mixing, thereby creating a bicontinuous state with more interfacial area than is required to accommodate all of the NNW particles,
stopping the mixing so that the NNW particles come into intimate contact on a continuous fluid-fluid interface, precipitating gel formation.

According to an inter-related tenth aspect of the present invention there is provided a method of making a Janus bead, comprising the steps of;
mixing together approximately equal quantities of spherical micelles comprising XZ and YZ block copolymers, wherein X, Y and Z are polymer chains, in a solution comprising approximately equal volumes of at least two solvents, immiscible at a defined temperature range, at a temperature range where the two solvents become miscible, and under such conditions that mixed micelles form spontaneously;
subsequently altering the temperature to a two-phase region where the solvents are immiscible, causing spinodal decomposition, thereby sequestering the block copolymers at an interface between the solvents;
maintaining a temperature such that the Z polymer chains remain above their glass transition temperature and the XZ and YZ block copolymers migrate to opposite sides of the micelle;
reducing the temperature such that the Z polymer chains pass through their glass transition temperature and the segregated micelle block copolymers are made stable, thus creating particles with hemispheres of opposite wetting properties.

According to an inter-related eleventh aspect of the present invention there is provided a method of making a Janus bead, comprising the steps of;
preparing a fluid-bicontinuous particle-stabilised gel; coating substantially one half of the particles in the fluid-bicontinuous particle-stabilised gel with substances that are dissolved in one or both of the first fluids and the second fluids.

BRIEF DESCRIPTION OF THE DRAWINGS

Various embodiments of the present invention will now be described by way of example only, with reference to the following drawings of which.

DETAILED DESCRIPTION OF PREFERRED EMBODIMENTS

Figure 1:
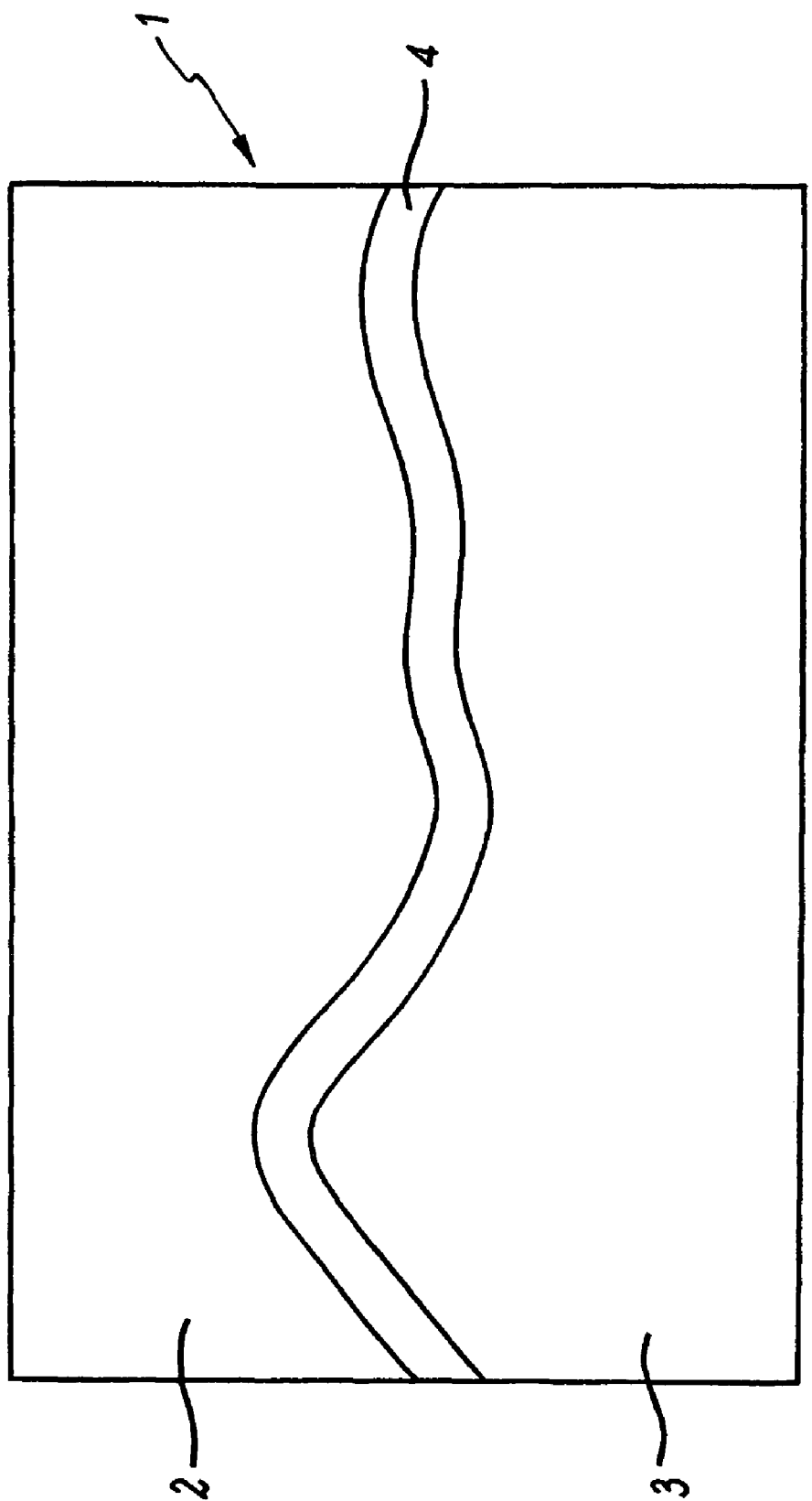
FIG. 1 is a two-dimensional schematic diagram of the fluid-bicontinuous particle-stabilised gel illustrating the local disposition of the first and second fluids and the solid film in accordance with an embodiment of the present invention.

Referring to FIG. 1, there is depicted a fluid-bicontinuous particle-stabilised gel 1 comprising a first continuous fluid 2, a second continuous fluid 3 and a stabilising particle layer 4. The first continuous fluid 2 and the second continuous fluid 3 are immiscible within a specific temperature range. The stabilising particle layer 4 is located at the interface between the first continuous fluid 2 and second continuous fluid 3. In this embodiment the fluid-bicontinuous particle-stabilised gel 1 is in a non-equilibrium arrested state such that it retains macroscopic rigidity, and such that the stabilising particle layer 4 is a rigid, arrested film of particles (hereafter called a "solid film"). Also, in this particular embodiment the first continuous fluid 2 is dodecane, the second continuous fluid 3 is ethanol and the stabilising particle layer 4 comprises silica beads (not shown). The solid film is made rigid by bonding interactions between particles (or colloids) (not shown) or alternatively by jamming of repulsive particles (not shown), the latter caused by the tendency of the fluid-fluid interface 6 to minimise its area.

The non-equilibrium arrested state, wherein the stabilising particle layer 4 is a solid film, affords certain characteristic properties to the fluid-bicontinuous particle-stabilised gels 1.

In particular, due to the presence of the stabilising particle layer 4 as a solid film, they are unaffected by the presence of external solvents. That is to say the fluid-bicontinuous particle-stabilised gels 1 will not be denatured or broken down by oil or water based solvents, as the first continuous fluid 2 and the second continuous fluid 3 are "trapped" in an interpenetrating domain by the stabilising particle layer 4.

In contrast to formulations based on compressed droplets (e.g. Pickering emulsion droplets), any increase in the volume of the first continuous fluid 2 or the second continuous fluid 3 results in an increase of the interfacial area between the first continuous fluid 2 and the second continuous fluid 3. This imparts an energy cost high enough to prevent swelling or dissolution of the fluid-bicontinuous particle-stabilised gel 1 by an external solvent (not shown), even when the external solvent comprises fluids identical to those present in the first continuous fluid 2 and/or the second continuous fluid 3. However it will not prevent permeation flows in which the first continuous fluid 2 and/or the second continuous fluid 3, either in pure form or containing solutes (not shown), are passed through the fluid-bicontinuous particle-stabilised gel 1, either sequentially or simultaneously, from the same or from different directions, without destroying the fluid-bicontinuous particle-stabilised gel 1. Such flow will allow intimate contact of two solutes (not shown), each soluble in the first continuous fluids 2 or second continuous fluids 3, at the fluid-fluid interface (not shown) within the fluid-bicontinuous particle-stabilised gel 1.

Figure 2:
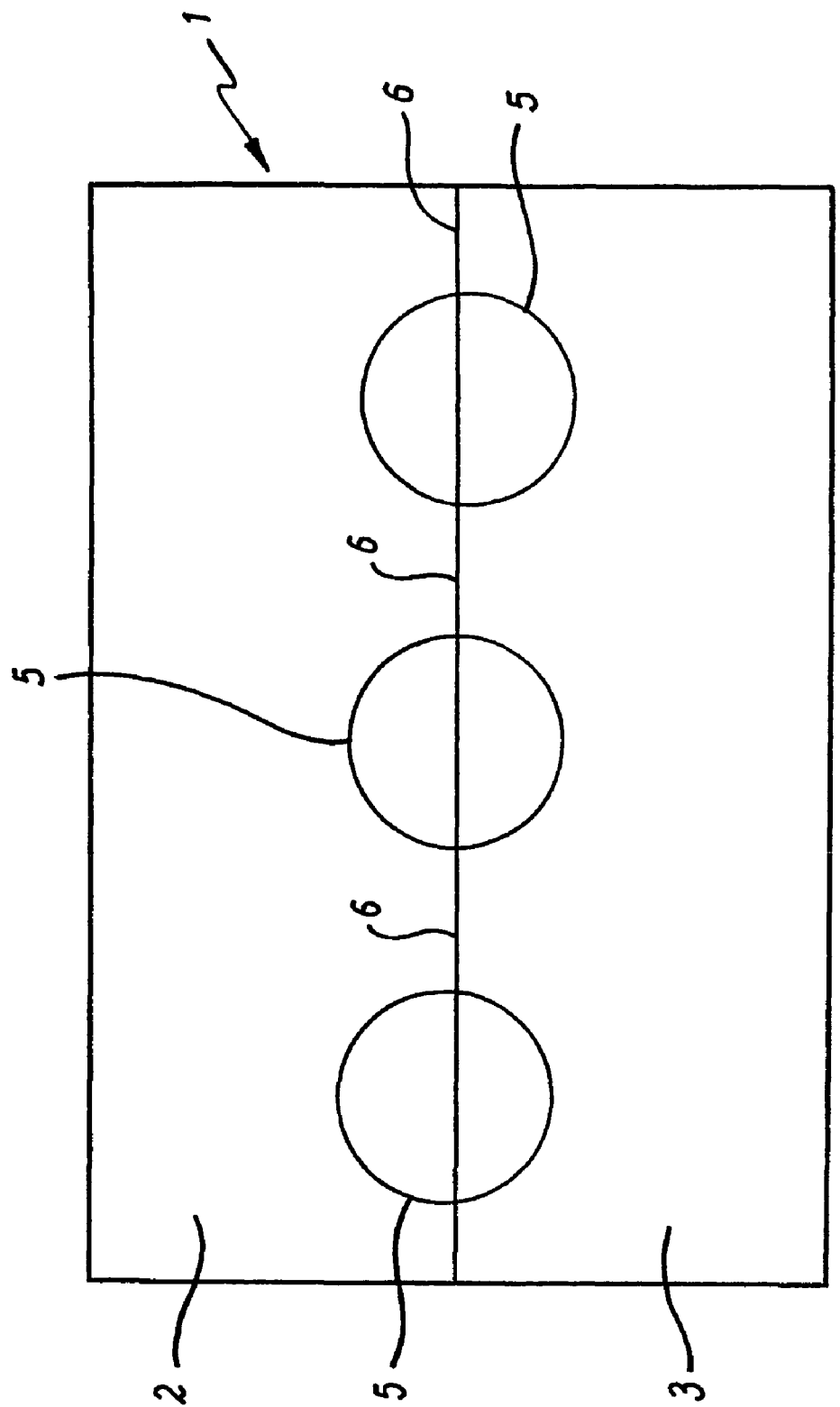
FIG. 2 is a two-dimensional schematic diagram of the near-neutral wetting particles of the continuous monolayer at the interface between the two fluid constituents of the fluid-bicontinuous particle-stabilised gel in accordance with an embodiment of the present invention.

Referring now to FIGS. 1 and 2, the stabilising particle layer 4 in the arrested state comprises NNW particles 5 in intimate contact. In this context, intimate contact means that the NNW particles 5 are either; physically touching, held apart by repulsive forces or, attracted to one another and held together by means of inter-molecular forces.

Although the afore-mentioned constituents may be combined to produce a fluid-bicontinuous particle-stabilised gel 1, it is noted that the first continuous fluid 2 may be any hydrophobic species and the second continuous fluid 3 may be any hydrophilic species, or vice versa. Furthermore, the fluid-bicontinuous particle-stabilised gel 1 may comprise a combination of any first continuous fluid 2 and any second continuous fluid 3 wherein the first continuous fluid 2 and second continuous fluid 3 are immiscible. Similarly, the stabilising particle layer 4 may comprise any suitable particle that will form a continuous stable layer at the interface between two fluids.

As shown in FIG. 2, the fluid-bicontinuous particle-stabilised gel 1 comprises a first continuous fluid 2, a second continuous fluid 3 and near-neutral wetting particles 5. The near-neutral wetting particles 5 are located at an interface 6 between the first continuous fluid 2 and the second continuous fluid 3. In this embodiment, the near-neutral wetting particles 5 are spherical units comprising a substantially uniform surface treatment creating a contact angle at the fluid-fluid-solid interface 6 of between 85 and 95 degrees.

In addition to NNW particles 5, partially wetting (PW) particles (not shown) of fluid-fluid-solid contact angle between 0 and 180 degrees can also be used. They are typically obtained by altering the treatment of the PW particles during preparation. However, NNW particles 5 are most effective because they are closest to the neutral wetting (NW) condition (where the fluid-fluid-solid contact angle is close to 90 degrees). The NNW particles 5 sit centrally on the interface 6, however a similar effect can be achieved by using Janus beads (not shown). A Janus bead is a substantially spherical colloidal particle with hydrophilic and hydrophobic hemispheres, separated by a sharply defined equator. When Janus beads are used the wetting properties are not neutral on either hemisphere but the meniscus is trapped at their junction. Furthermore, Janus beads with unequal areas of opposite wetting properties can be used. These sit off centre, with the dividing line between the two areas situated on the interface 6.

The best stabilising effect is found at a contact angle between 85 and 95 degrees, as this is closest to the neutral wetting angle of 90 degrees, although it has been found that a contact angle between 75 and 105 degrees confers adequate stability to the fluid-bicontinuous fluid-stabilised gels. It will be appreciated, however, that the NNW particles can have a contact angle between 70 and 110 degrees, or between 60 and 120 degrees.

FIG. 2 illustrates the presence of NNW particles 5 of a single wetting angle only. However, it will be understood that particles with different wetting angles can be incorporated into the same fluid-bicontinuous particle-stabilised gel 1.

Various NNW particles 5 can be used. For example, the NNW particle 5 could be a colloidal particle with a mixed polymer surface comprising flexible chains of two types, A and B, (not shown) substantially uniformly spread across the NNW particle 5 surface and grafted to the surface at one end. A and B are chosen so that the first continuous fluid 2 has an affinity for A, and the second continuous fluid 3 has an affinity for B, or vice versa. For given solvents, fractions of A and B can be tuned to aid near-neutral wetting. Furthermore, by making the flexible chains A and B relatively long, the less favoured chain will disperse in each solvent so that the NNW particle 5 presents a different surface on either side of the interface 6. This will reduce both of the solid-fluid interfacial tensions, causing NNW particles 5 to adopt a near-neutral wetting position at the fluid-fluid interface 6 within the fluid-bicontinuous particle-stabilised gel 1.

A further choice of NNW particle 5 is a spherical micelle, comprising an equal mixture of XZ and YZ block copolymers (not shown), wherein X, Y and Z are polymer chains, with Z insoluble in both solvents (for example, a fluorocarbon). Under some conditions such mixed micelles, driven by mixing entropy, will form spontaneously. When such micelles are prepared in a solvent mixture at a temperature where the solvents are miscible, and are subsequently quenched into a two-phase region where the solvents are immiscible, then they will be sequestered at the interface 6 as NNW particles 5. Furthermore, so long as the Z chains remain above their glass transition temperature, the XZ and YZ blocks will migrate to opposite sides of the micelle. This results in a NNW particle 5 wherein the contact angle is directly controlled by the relative amounts of X and Y. Therefore a NNW condition is effectively achieved whenever near-equal areas of X and Y chains are present after segregation within the micelle. If the Z chains pass through their glass transition temperature the segregated NNW particles 5 are made stable. Such NNW particles 5 permanently present two different hemispheres of opposite wetting properties and therefore become Janus beads.

An alternative way of producing Janus beads is to prepare a fluid-bicontinuous particle-stabilised gel and then coat substantially one half of the NNW particles 5 with substances that are dissolved in one or both of the first fluids 2 and the second fluids 3. This can be done by precipitating a substance such as (but not limited to) a metal, onto the NNW particles 5 surface. However, it is appreciated that several other substances are suitable for precipitating onto the NNW particles 5, and for making Janus beads using this method.

The NNW particles 5 can be colloidal particles with micro-heterogeneous wetting properties at different patches on their surfaces. The NNW particles 5 can also be globular biomolecules or, more specifically, globular proteins. The colloidal particles can possess attractive (bonding) interactions, providing added stability to the stabilising particle layer 4 at the fluid-fluid interface 6.

The fluid-bicontinuous particle-stabilised gels 1 can also comprise emulsion droplets, in a fluid or aggregated state, within one or both of the first continuous fluids 2 and second continuous fluids 3.

The fluid-bicontinuous particle-stabilised gels 1 can also comprise a plurality of interpenetrating domains (not shown), which comprise a multicontinuous fluid or gel structure; wherein the fluid-bicontinuous particle-stabilised gels 1 are simultaneously permeable to a plurality of mutually immiscible fluids. The multicontinuous fluid or gel structure can comprise fluid-bicontinuous particle-stabilised gels 1.

As shown in FIGS. 1 and 2, a fluid-bicontinuous particle-stabilised gel 1 has a first continuous fluid 2 and a second continuous fluid 3 in intimate contact at an interface 6 by means of a particle-stabilised continuous monolayer 4 in the arrested state, comprising near-neutral wetting particles 5 that span the interface 6. Fluid-bicontinuous particle-stabilised gels 1 of this type are highly tunable and can be prepared for specific applications. In particular the shear modulus, the pore size and the yield stress (and thus the macroscopic rigidity) can be varied by altering the volume ratios of the first continuous fluid 2 and the second continuous fluid 3, and by varying the relative amount of, and the size of, the near-neutral wetting particles 5 that are incorporated. In addition, the properties of the fluid-bicontinuous particle-stabilised gels 1 can also be varied by altering the method of preparation (or the process history), and the presence or absence of bonding interactions between the colloidal particles.

The fluid-bicontinuous particle-stabilised gels 1 are robust against attack by external solvents whilst remaining simultaneously permeable to such external solvents (including, but not limited to, solvents identical to the first continuous fluid 2 and the second continuous fluid 3). They are also permeable to fluids that are soluble in the first continuous fluid 2 and the second continuous fluid 3. The fluid-bicontinuous particle-stabilised gel 1 can therefore provide a means for intimate contact between two immiscible liquids (not shown) allowing solutes in the two liquids to come into contact for the purposes of, for example, a chemical reaction.

Furthermore, the fluid-bicontinuous particle-stabilised gels 1 can comprise fluid domains with characteristic length scale (or pore size) that is readily tunable by formulation, as will be described in more detail below.

The high tunability of the fluid-bicontinuous particle-stabilised gels 1 allows them to be used in various applications. In particular, the high interfacial area and adjustable pore size makes the fluid-bicontinuous particle-stabilised gels 1 excellent media for heterogeneous catalysis and/or chemical reactions, in which two species, one soluble in each fluid, can enter the gel and encounter each other at those parts of the fluid-fluid interface 6 that are not covered by particles (specifically at the interstices between the particles comprising the solid film). Also, fluids can be pumped in opposite directions through the fluid-bicontinuous particle-stabilised gels to create a reaction medium or catalytic support.

Furthermore, a fluid-bicontinuous particle-stabilised gel 1, wherein the first continuous fluid 2 or the second continuous fluid 3 is a fluid of high thermal conductivity (such as water), itself displays high thermal conductivity, particularly in comparison to any gel in which that fluid is not continuous. The thermal conductivity is approximately 30 to 40 percent of the thermal conductivity of water or whatever is the more thermally conducting solvent.

The tunability also allows that the fluid-bicontinuous particle-stabilised gels 1 may be specifically prepared for applications such as, but not limited to, personal care formulations, foodstuffs, drilling muds and pharmacological uses.

Other properties can also be incorporated into the fluid-bicontinuous particle-stabilised gels 1 by means of altering the first continuous fluid 2, the second continuous fluid 3 or the near-neutral wetting particle 5. By altering the constituent parts and process history of the fluid-bicontinuous particle-stabilised gels 1, the macroscopic structure is also affected. In some cases the fluid-bicontinuous particle-stabilised gels 1 may become fully ordered (three-dimensional periodic) and in others an amorphous arrangement of the two interpenetrating domains exists. Ordered and/or amorphous structures created in this way, comprising two solvents of very different refractive index, have very useful optical properties that are not limited to, but may include photonic band-gaps. These functional and optical properties are further tunable by varying the refractive index of the NNW particles 5 and/or by using NNW particles 5 that are magnetic or that have electrical conductivity. In particular the particles can be superparamagnetic as described in the embodiment below. The optical properties can also be changed by adjusting the formulation of the fluid-bicontinuous particle-stabilised gels 1.

In one particular embodiment the properties of the fluid-bicontinuous particle-stabilised gel can be altered using magnetism. In this embodiment the near-neutral wetting particles are made superparamagnetic. Such particles behave normally in the absence of a magnetic field, but in the presence of a magnetic field, they develop strong magnetic moments. Under suitable conditions, these particles can be removed from the interface by the magnetic field. This enables a solid gel phase to be rendered entirely fluid by switching on a magnetic field.

The fluid-bicontinuous particle-stabilised gels 1 can comprise a first fluid 2 and a second fluid 3 of different refractive index, wherein the first fluid and the second fluid have a ratio of refractive indices greater than 2; and the first fluid 2 having a refractive index lower than the second fluid 3, or vice versa. Optical properties are best achieved when the first fluid 2 and the second fluid 3 of different refractive index have a ratio of refractive indices that is as high as possible. Therefore it is recognised that fluid-bicontinuous particle-stabilised gels 1 with a first fluid 2 and a second fluid 3 with ratios of refractive indices greater than 3 will also have useful optical properties. Whilst the preferred embodiment has a ratio greater than 2, acceptable gels can be formed that have a ratio of less than 2.

The optical properties can be further modified or improved by evaporating one or other of the first continuous fluid 2 or the second continuous fluid 3, thereby replacing it with air or vapour of lower refractive index than the original fluid. The optical properties can also be further modified or improved by deposition of silicon or another high refractive index material in place of the air, and/or by removing the colloidal particles, in addition to one of the fluids, by etching. These templating operations can also be enabled by freezing the fluid-bicontinuous particle-stabilized gel to create a solid-bicontinuous structure prior to etching and/or evaporation.

The fluid-bicontinuous particle-stabilised gel 1 properties can also be altered by replacing or converting one or both of the first continuous fluids 2 and second continuous fluids 3 into a solid, vapour or gas while retaining the mechanical integrity and the topology of the original structure.

As shown in FIG. 2, the NNW particles 5 sequestered at the interface 6 can be manipulated such that the fluid-fluid-solid contact angle is deliberately deviated from the NNW angle. This is done, for example, by varying the relative amounts and size of X and Y when the NNW particles 5 are spherical micelles comprising XZ and YZ block copolymers (not shown), with Z insoluble in both solvents (for example, a fluorocarbon). The same effect is achieved by homogeneous surface treatment of colloids such as silica spheres to achieve the required contact angle.

Deliberately deviating from the neutral wetting condition imparts a spontaneous curvature to the interface 6. This spontaneous curvature can be used to counterbalance the tendency of bicontinuous states to curve towards the minority phase, which can result in the loss of bicontinuity at strongly asymmetric phase volumes of the two solvents. Therefore, strongly fluid asymmetric, but nonetheless fluid-bicontinuous states can be created. In this context, "fluid asymmetric" is understood to mean that there is an excess of one fluid relative to the other. Fluid-bicontinuous particle-stabilised gels 1 of this type have a larger surface area per unit volume at the fluid-fluid interface 6, due to the eccentric placing of the near-neutral wetting particles 5 with respect to the interface 6. This feature improves the fluid-bicontinuous particle-stabilised gels 1 performance as a heterogeneous catalyst support or as a precursor of a heterogeneous catalyst support. Also, deliberately using particles which have a mixture of two different wetting angles can induce curvature in the particle laden surfaces via the local concentrations of each type of particle.

Illustrated in FIGS. 1 and 2, is a fluid-bicontinuous particle-stabilised gel 1 comprising a percolating stabilising particle layer 4, which imparts both a static modulus and a yield stress to the fluid-bicontinuous particle-stabilised gel 1. In one embodiment of the invention, all of the NNW particles 5 reside on the interface 6. The static modulus and yield stress are approximately 1000 Pa and 100 Pa respectively. This fluid-bicontinuous particle-stabilised gel 1 will remain self-supporting under the forces of gravity for a first continuous fluid 2 and a second continuous fluid 3, mismatched in density by approximately 10 percent, to a height of over 10 cm.

A further embodiment of the fluid-bicontinuous particle-stabilised gel 1 with a yield stress of approximately 10,000 Pa has the capacity to support relatively heavy objects indefinitely against the force of gravity. For example it may suspend rock cuttings, from drilling, that are several centimeters across in size.

This can be usefully combined with the property of reversible fluidization. In reversible fluidization, the macroscopic rigidity of the fluid-bicontinuous particle-stabilised gels 1 is lost when the fluid-fluid interfacial area of the interface 6 is caused to expand by more than about 30 percent. When this situation arises, the rigidity of the stabilising particle layer 4 is lost and the stabilising particle layer 4 can flow. This will arise for repulsive colloids. It will also arise for attractive colloids within the stabilising particle layer 4 if these are not bonded together too strongly. Interfacial expansion will occur under bulk stress so that fluid-bicontinuous particle-stabilised gels 1 will be strain-softening. Once the yield stress is exceeded, the fluid-bicontinuous particle-stabilised gels 1 will become substantially fluidised, wherein the fluidization is reversible (to the re-arrested state). This will have several applications including drilling muds and personal care products, where reversible fluidization is required.

In a further embodiment of the invention, the resulting re-arrested state remains anisotropic. In this case shearing may produce a state consisting of droplets, parallel flat layers or cylinders, in all cases particle-stabilised, whose properties on re-arrest are significantly different from the original state. This allows the fluid-bicontinuous particle-stabilised gels 1 to be used as "flow to structure" gels with particular properties. The re-arrested state can have a different morphology from the initial state.

The fluid pathways, the extensive interface and the novel elastic properties of the fluid-bicontinuous particle-stabilised gel can all be employed separately or in combination. For example, in a further alternative embodiment, the fluid-bicontinuous particle-stabilised gel structure is made permanent at all temperatures by cross-linking the colloids. This can be easily realised for polymer based colloids.

In a still further alternative the particles are further functionalized for applications in catalysis. Possible applications could involve objects or chemicals transferred across the interface between the fluids. Such processes can be traced using fluorescent tracers and confocal microscopy.

Figure 3:
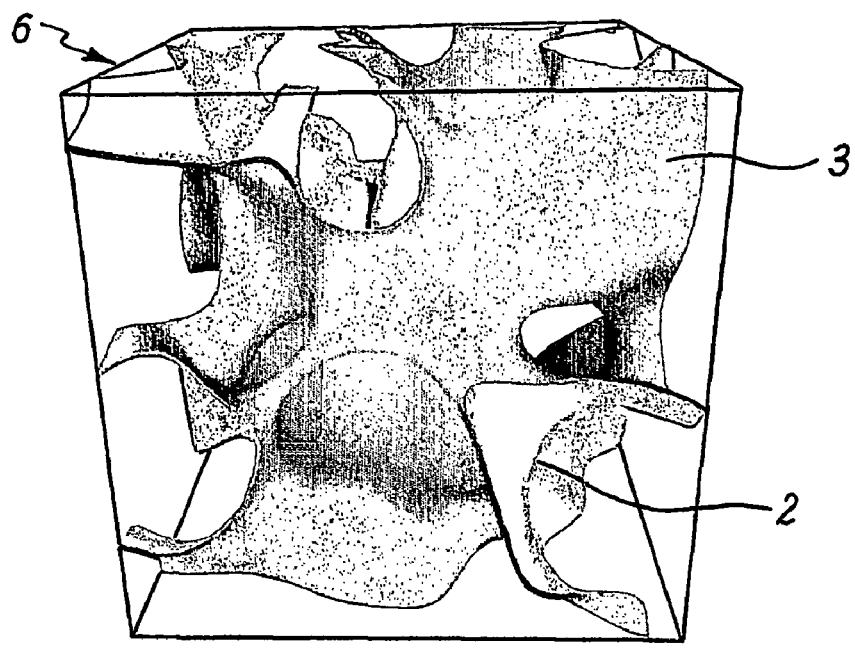
FIG. 3 is a three-dimensional computer-generated image of the interface between the two bicontinuous fluids in accordance with an embodiment of the present invention.

Referring to FIG. 3 there is shown an image of an interface 6 between a first continuous fluid 2 a second continuous fluid 3.

Figure 4:
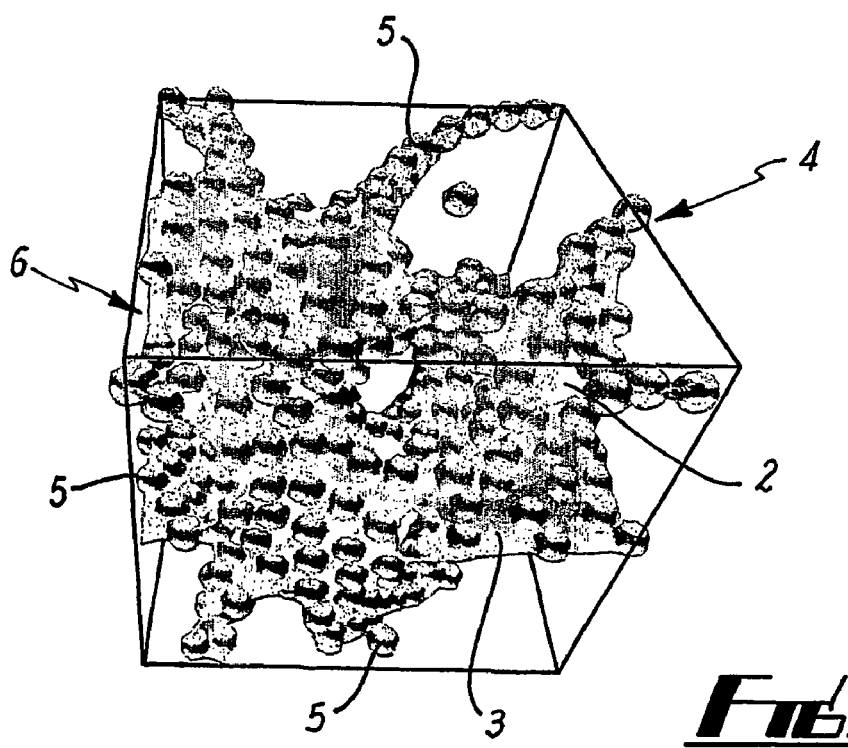
FIG. 4 is a three-dimensional computer-generated image illustrating the global topology of the continuous stabilising particle layer in the arrested state in accordance with an embodiment of the present invention.

Referring to FIG. 4 there is illustrated an image of a continuous stabilising particle layer 4 in the arrested state, as it exists on an interface 6 between the first continuous fluid 2 and the second continuous fluid 3. Also illustrated are NNW particles 5 sequestered at the interface 6.

The method of preparation of the fluid-bicontinuous particle-stabilised gels of FIGS. 1 to 4 will now be described. The method involves dissolving the NNW particles 5 in a binary solution (comprising roughly equal volumes of two immiscible solvents) in a temperature range where the two solvents become miscible. The temperature is then quenched into the two-phase region, causing spinodal decomposition (transition from a single phase to two phases). Early in this process, the moving interfaces 6 "sweep-up" the NNW particles 5 and create the bicontinuous structure with some or all of the NNW particles 5 on the interface 6. That is, as the fluids begin to separate the NNW particles 6 move to the interface 6 between the two fluids. The fluids continue to separate until the interface 6 is completely coated with NNW particles 5. After quenching, the NNW particles 5 on the interface 6 progress toward, and after a period, come into intimate contact (creating the arrested state), so forming a fluid-bicontinuous particle-stabilised gel 1.

Figure 5A:
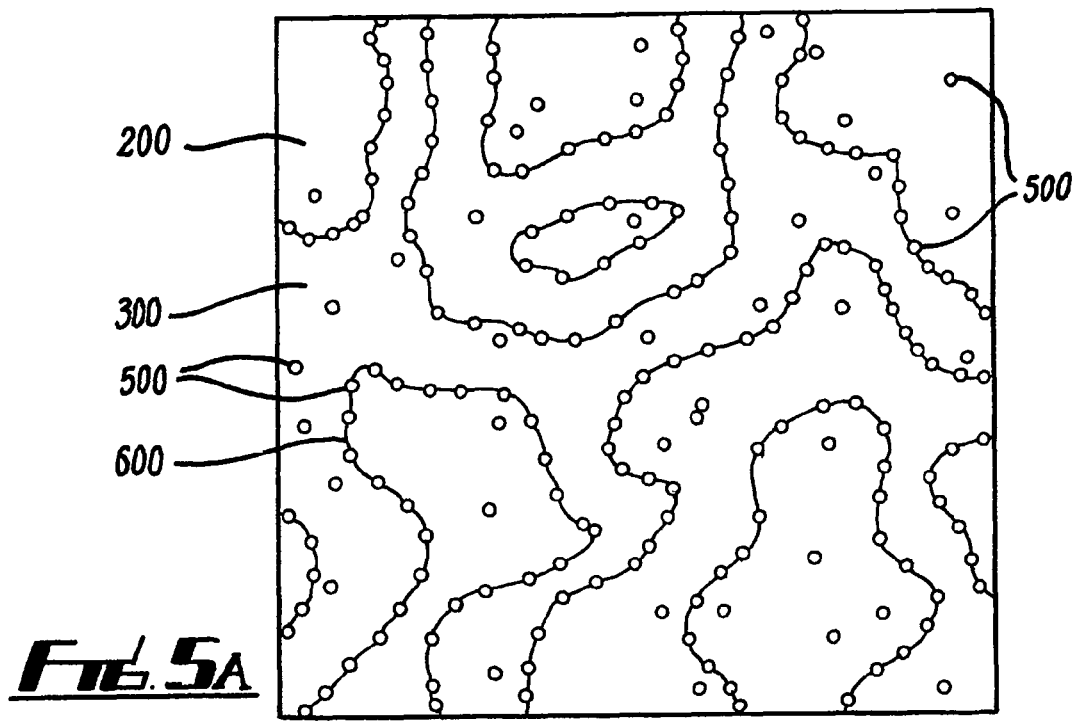
FIGS. 5A and 5B show a first and second fluid and particles amassing on the interface between the first and the second fluids as a fluid-bicontinuous particle-stabilised gel forms.
Figure 5B:
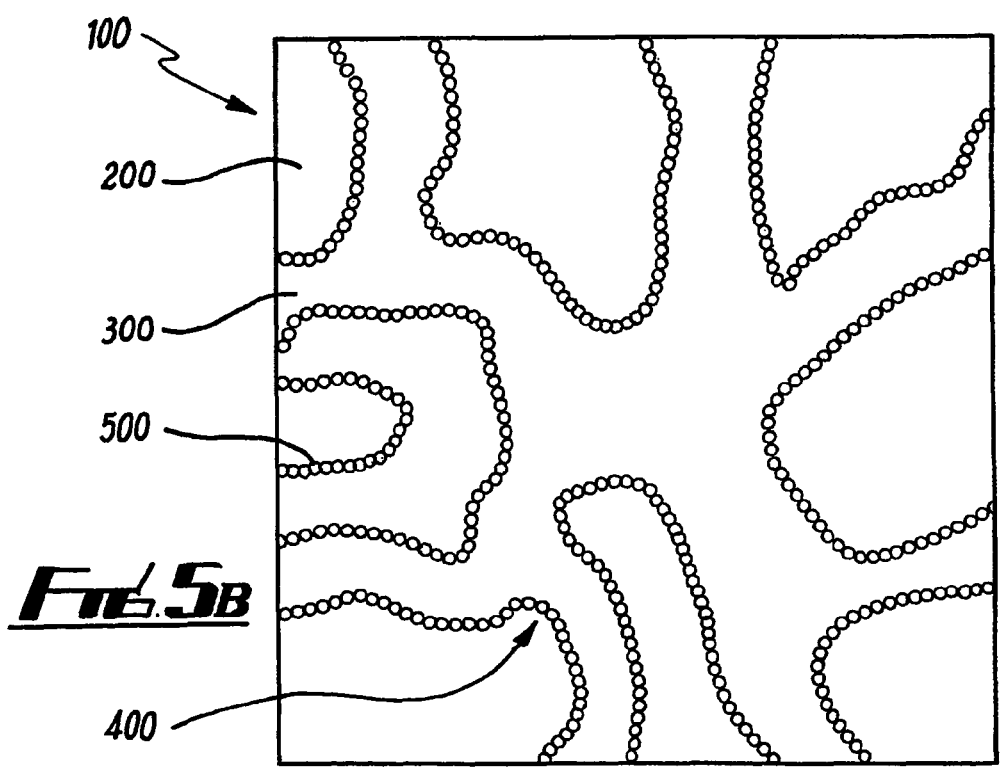

Referring now to FIGS. 5A and 5B, there is illustrated a further embodiment in which a fluid-bicontinuous particle-stabilised gel 100 is prepared according to the procedure as outlined below. Two immiscible fluids, in this case methanol 200 and hexane 300, are heated such that they may mix sufficiently. Silica colloid particles 500 with specially modified surface chemistry and with a diameter of 0.5 µm are then dispersed at this elevated temperature, at which the fluids form a single phase (not shown). The surface chemistry is modified to yield roughly 90 degrees near neutral wetting angle with methanol 200 and hexane 300. The mixture is then cooled very quickly using a dry ice bath (not shown); although it will be appreciated that cooling can be done in a variety of ways. On fast cooling, the fluids separate via a large scale instability known as spinodal decomposition. The interface 600 is pinned with particles while this separation is underway. FIG. 5A shows the fluids beginning to separate; the colloidal particles 500 reduce the system's energy by sitting on the interface 600 between the two fluids. The fluids continue to separate (and hence reduce their shared interface) until the interface 600 is completely coated with colloidal particles 500, as in FIG. 5B. In FIG. 5B, methanol 200 and hexane 300 are continuous fluids, separated by a stabilising particle layer 400 which contains colloidal silica particles 500 which span the interface (not shown) between the two fluids.

In the example given the fluids are methanol and hexane, however, it will be appreciated that any suitable combination of solvents can be used. For example, it has been shown that ethanol and dodecane can also be used to achieve a similar result. Also, whilst in the example given the particles used are colloidal silica particles with a diameter of 0.5 μm, it will be appreciated that any suitable particles can be used.

Other combinations of solvents and particles can also be used. For example, the two fluids can be a hydrocarbon and a fluorocarbon with the interface being stabilised by partially fluorinated polymer colloid particles.

Figure 6:
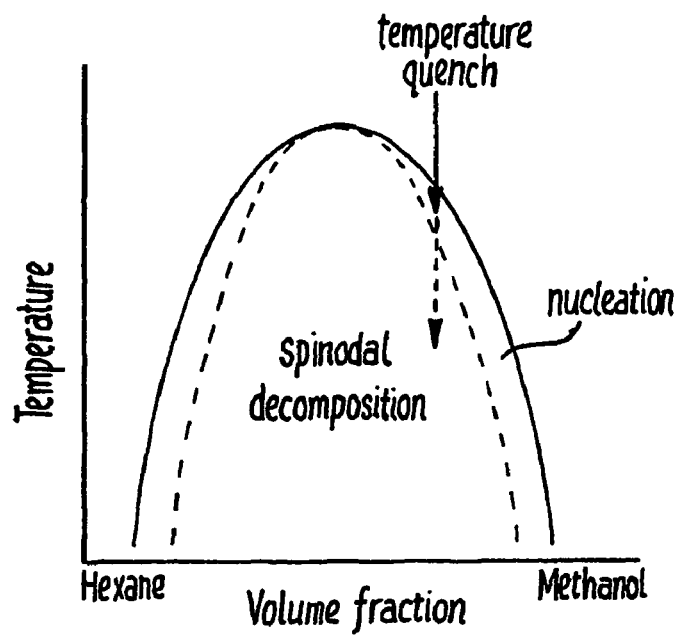
FIG. 6 is a phase diagram for methanol and hexane which illustrates the mixing of the two compounds with temperature.

Referring now to FIG. 6, there is shown a phase diagram for methanol and hexane which illustrates that these two fluids have a heat-dependent mixing characteristic as is required in the method as described above. Specifically, the diagram illustrates that performing a temperature quench at a suitable volume fraction and temperature will produce spinodal decomposition.

An alternative method of preparation is to vigorously disperse the NNW particles in a mixture of two solvents at high shear rate. In strong enough flows the two solvents will mix intimately creating a bicontinuous state with more interface than required to accommodate all of the NNW particles present. The flow is then stopped and the fluid-bicontinuous particle-stabilised gel forms as the NNW particles come into intimate contact on the interface.

Computational Proof of Principle

The specific examples, such as the methanol, hexane, silica colloid fluid-bicontinuous particle-stabilised gel, as described above are real materials and have been prepared in the laboratory. However, to augment these laboratory findings, there is presented below computational proof which illustrates how fluid-bicontinuous particle-stabilised gels can form and exist.

Here it is established by computer simulation a previously unexplored kinetic pathway that enables the creation of a new class of amorphous soft-solid materials—fluid-bicontinuous particle-stabilised gels. As alluded to previously, in these materials a pair of interpenetrating, bicontinuous fluid domains are frozen into a permanent arrangement by a densely jammed monolayer of colloidal particles at the fluid-fluid interface. One possible application, explored below, is as a cross-flow microreaction medium in which two immiscible fluids are continuously brought into intimate contact by pumping them in opposite directions through a static fluid-bicontinuous particle-stabilised gel.

To achieve maximal stability of a particle-stabilized interface, the colloidal particles should be chosen with nearly equal affinity for the two liquids involved. This creates similar values for the two fluid-solid interfacial tensions, and thus a fluid-fluid-solid contact angle close to 90 degrees (neutral wetting). A spherical particle is then in stable equilibrium with its equator at the fluid-fluid interface. In practice, this equilibrium is so stable that detachment of such a particle cannot be achieved by thermal motion alone. Indeed, for neutral wetting, the fluid-solid interfaces have the same total energy regardless of particle position, but the fluid-fluid interfacial area is reduced, by a disc of radius a, when the particle lies midway across the interface. The detachment energy $\epsilon$ is the interfacial energy of this disc $\epsilon = \sigma \pi a^2$, with $\sigma$ the fluid-fluid interfacial tension. Hence $\epsilon/k_B T = (a/a_0)^2$ where $a^2_0 = k_B T/\pi \sigma$. For T=300 K and typical $\sigma$ of order 0.01 Nm$^{-1}$ or larger, $a_0$ is 0.4 nm or less. Thus $\epsilon/k_B T \geq 10$ even for a particle of 1 nm radius, and thermally activated detachment can be safely neglected for, say, $a \geq 3$ nm.

Suppose now that near-neutral wetting particles are suspended in a binary solvent under conditions where the fluids are fully miscible (generally at high temperature) and of roughly equal volume fraction. In the absence of strong attractions between them, the particles will diffuse freely. However, if the temperature is now quenched deep into a two phase region, the solvents will demix by spinodal decomposition, as described previously. A sharp interface between the two fluids soon develops, and coarsens. During the coarsening, which is driven by the tendency of the interface to reduce its area, the characteristic lengthscale L(t) initially increases with time in a well-understood manner, causing bumps on the interface to flatten, and causing necks between neighboring domains of the same fluid to pinch off.

What happens next has been studied using lattice-Boltzmann (LB) simulations. It has been found that as coarsening proceeds, the interface sweeps through the fluid phases, efficiently collecting the colloidal particles which are then sequestered upon it. Initially the attached particles have little effect on the interfacial motion, but as more are collected and the interfacial area shrinks, they soon approach a densely packed monolayer. At this point, the fluid must either (i) stop coarsening at some lengthscale. L(t)=L* or (ii) thereafter expel particles steadily from the ever-shrinking interface. In these simulations, there is evidenced a drastic curtailment of the coarsening and rather little particle expulsion. This suggests that the free energy landscape of the dense colloidal film is such as to trap particles, rather than assist their expulsion.

The parameter values chosen for these runs map onto particles of radius a=5 nm in a symmetric pair of fluids each having viscosity $\eta = 10^{-3}$ Pa s and mass density $\rho = 10^3$ kg m$^{-3}$, with $\sigma = 6 \times 10^{-2}$ Nm$^{-1}$ at T=300 K; such values are typical of a short-chain hydrocarbon/water or alcohol/water mixture. The particles have purely repulsive interactions, with range extending somewhat beyond their hard-sphere (hydrodynamic) radii, so that particles remain visibly separated even in a dense monolayer. The parameter mapping is made by matching dimensionless control groups $\epsilon/kT$ and $a\rho\sigma/\eta^2$. Brownian motion of the colloidal particles is included, but has rather little effect, and would have even less effect with larger particles. It has also been checked the role of short-range, thermally reversible bonding among colloids, but this too has little effect. Both observations confirm the strong separation between Brownian and interfacial energy scales.

These simulations are the first of their kind and are the largest and most accurate achievable with current resources; but some numerical compromises are inevitable. (Larger runs would be achievable in two dimensions, but the physics of fluid bicontinuity is then radically compromised.) First, the Reynolds number Re=(dL/dt)$\rho$a/$\eta$ is much larger than in the real system, though there still is Re<<1. More importantly, the scale separation between the particle radius a and the fluid-fluid interfacial thickness $\xi$ is only modest (a factor two or three), with the lattice spacing, in turn, not much less than $\xi$. In these simulations, the particles in a narrow neck can thus become so closely packed that the interstitial areas of fluid-fluid interface are improperly discretized, under-representing the energy barrier to short-scale rearrangements. Finally, for the physical parameters given above, the effective run-time of the largest simulations is only about 300 ns, far short of the time scales required to positively identify a material as a macroscopically arrested gel. (For larger particles, say a=3 μm, the equivalent run time would be around 5 ms.)

Figure 7:
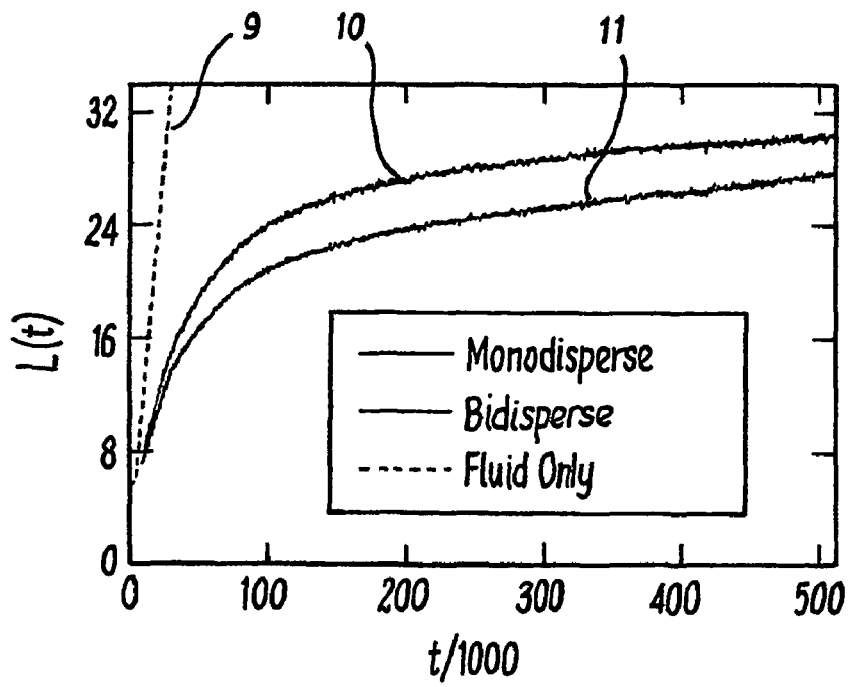
FIG. 7 is a graph that illustrates the time evolution of the structural length during the formation of a gel.

Hence, although these direct simulations confirm the proposed kinetic pathway for creating a fluid-bicontinuous state with particle laden interface, they cannot tell us whether this state is a fully arrested fluid-bicontinuous particle-stabilised gel on laboratory time scales. However, these observations, particularly for bidisperse particles, are consistent with the idea that arrest does finally occur despite the residual late-time dynamics visible in the L(t) curves of FIG. 7. FIG. 7 is a graph illustrating time evolution of the structural length scale L(t) for monodisperse (line 11) and bidisperse (line 10) particle runs (measured in lattice units). Without particles coarsening would proceed with the slope indicated by line 9. Near-arrest is visible, suggesting a finite asymptotic domain size L*, particularly in the bidisperse case, which is line 10. This L* is less than ¼ of the simulation box size and not limited by finite-size effects. For the parameter values chosen (corresponding to 5 nm particles) the data shown run approximately from 6 ns to 300 ns in real time, with L*≈70 nm. (At times less than 6 ns, the fluids are demixing diffusely so that sharp interfaces are yet to form.) The remaining line 11 corresponds to the monodisperse case.

In common with other arrested states such as glasses, fluid-bicontinuous particle-stabilised gels might show slow aging behavior in the approach to a saturated L(∞)=L*. Alongside aging, the slow residual coarsening could be due to the incomplete separation of length scales in LB noted above or, in the monodisperse case, due to a tendency for the interfacial layer slowly to acquire local crystalline order. (Such ordering would not preclude, and might even enhance, eventual structural arrest.) It has also been assessed the particle mobility in the interfacial film by measuring the distribution of individual particle displacements at late times. This was found to be dominated by the residual aging of the structure rather than by diffusion within the film. This supports the view that the film is akin to a two-dimensional glass in which particle diffusion is suppressed.

Further support for this view was gained by additional, higher-resolution LB runs that examine the dynamics of two specific structural motifs characteristic of the bicontinuous structure. One of these is a long cylinder (representing a fluid neck); without particles the Rayleigh-Plateau instability would cause the cylinder to break into droplets. It has previously been found that a disordered surface coating of monodisperse particles can suppress the instability; a finite amplitude perturbation of the interface does not grow but instead restructures the surface layer into a highly ordered solid film. A higher-resolution LB was run for a dense bidisperse colloidal packing on a cylindrical interface. When perturbed this shows no sign of either ordering or breakage, and the initial perturbation visibly decays, rather than grows. The structure arrests before the decay is complete; it persists at least four times longer than the time to rupture, $\tau_r$, of an unprotected cylinder. For $t \geq \tau_r$, no large scale motion is seen.

The second structural motif is a periodically undulating surface, roughly characteristic of a non-necklike section of the bicontinuous surface structure. Without particles, this would rapidly be pulled flat by interfacial tension. This process is interrupted by interfacial jamming: bumps persist at least a 100 times longer than without particles, with negligible macroscopic motion visible after an initial transient leading to the jammed state.

These higher-resolution results show that, at sufficient interfacial coverage, both necks and bumps can arrest by jamming of the adsorbed colloidal layer into a glass-like state. Since these two structural elements (the cylinder, with an unstable growth mode, and the ripple, with a stable decay mode) are in combination the driving features of bicontinuous coarsening, arrest of either would be enough to prevent coarsening. Hence these studies provide very strong supporting evidence for eventual structural arrest of the bicontinuous structure, caused by a jamming transition of the colloidal monolayer, in which the confining stress provided by the fluid-fluid tension causes it to solidify.

Once the interfacial film is indeed arrested, since it percolates in three dimensions, the entire material will acquire solid elasticity at scales beyond L*. The static modulus G of the resulting gel should scale with the interfacial energy density σ/L; so long as nearly all particles end up on the interface, L*~a/Φ with Φ the particle volume fraction. For τ=0.01 Nm$^{-1}$, $0.01 \leq \Phi \leq 0.1$ and 5 nm<a<5 μm it is estimated that $20 \leq G \leq 2 \times 10^5$ Pa. This is a very wide 'tuning' range for material design. Under nonlinear stress the interfacial area will dilate significantly: only a modest dilation (say 10%) may suffice to cause melting of the particle layer and drastic fluidization. This might instigate both flow and coarsening above some yield stress Y≈0.1 G. If the stress falls back below Y, it is expected that resolidification will occur, possibly with remnant anisotropy (hysteresis). The nonlinear flow behavior of these gels could thus show a remarkable strain-melting, possibly reminiscent of a colloidal glass, but with a much higher stress scale set by interfacial not Brownian forces. The estimates above for the material properties of the gel stem from the jamming of colloids by the interfacial forces and apply even for purely repulsive particles. Any additional bonding attraction, if of sufficient strength, might enhance the rigidity of the interfacial layer, but also risks colloidal aggregation within the bulk phase(s) prior to monolayer formation. Fusing the colloids after gel formation (e.g. by irradiation) would completely stabilize the structure and drastically alter the flow behavior.

Alongside bulk elasticity, it is expected that fluid-bicontinuous particle-stabilised gels will have several further interesting physical properties. First, the fluid-bicontinuous state should remain equally insoluble on exposure to either of its solvents. This contrasts with particle-stabilized emulsion gels formed by compression, in which an excess of the continuous phase could cause droplets to separate, losing macroscopic rigidity. (In fluid-bicontinuous particle-stabilised gels this will not happen, since neither of the two interpenetrating fluids can alter its volume without also increasing the total interfacial area.) The fluid-bicontinuous particle-stabilised gels can thus metastably support simultaneous coexistence with bulk phases of both fluids. This is reminiscent of an equilibrium property of middle-phase microemulsions, which in contrast to fluid-bicontinuous particle-stabilised gels are not gel phases but inviscid fluids as a result of their high interfacial mobility.

Second, fluid-bicontinuity imparts high permeability of the gel to either of its component solvents, and any reagents dissolved in them. Accordingly fluid-bicontinuous particle-stabilised gels have potential as media for continuous-process microreactions. Specifically, a static gel could support a steady permeation flow of both fluids simultaneously in opposite directions. This would bring two molecular reagents, soluble only in mutually immiscible fluids, into intimate contact at the fluid-fluid interface in the interstitial regions between the colloids. Products soluble in either phase would be swept out continuously. To test this concept, a LB simulation was run in which the two fluids are moving through the structure in opposite directions. On the timescale of the simulation, the gel has easily enough mechanical integrity to sustain this cross-flow without breaking up. Within the mapping onto physical parameters made previously, the chosen cross-flow fluid velocity v=0.01σ/η is of order 10 cm s$^{-1}$: this is an extremely large value, given the pore scale L* of order only 70 nm. Local shear rates are of order $10^6$ s$^{-1}$.

In summary, there is presented simulation data showing formation of a self-assembled bicontinuous structure with interfacially sequestered particles. This followed a novel kinetic pathway involving a colloidal suspension in a binary solvent, initially miscible, that undergoes a temperature quench. The simulations show a drastic curtailment of coarsening, consistent with an ultimate complete arrest of the structure: a scenario further supported by higher-resolution studies of appropriate structural motifs (bumps and necks). This suggests a route to the creation of new class of gels, fluid-bicontinuous particle-stabilised gels, with potentially remarkable physical properties.

Deviations from the neutral wetting angle introduces a tendency to form discrete droplets rather than the bicontinuous state, although this can partly be overcome by varying the quench rate, and preliminary studies suggest that contact angles between 80 and 100 degrees all behave similarly. Further information relating to the simulations is included below.

In the simulations reported here, for simplicity a perfectly symmetric pair of fluids with equal density $\rho$ and viscosity $\eta$ was chosen. The phase diagram that controls their demixing is also symmetric, being described by the free energy functional $$F[\Psi]=A\Psi^2/2+B\Psi^4/4+\kappa(\nabla\Psi)^2/4 \qquad (1)$$

(1) where the order parameter $\Psi$ describes the fluid composition, and the choice of the parameters A, B and $\kappa$ controls the fluid-fluid interfacial tension $\sigma$ and thickness $\xi$.

The two solid-fluid interfacial tensions are exactly equal, and the interfacial thermodynamics implemented as reported by K. Stratford, R. Adhikari, I. Pagonabarraga, and J.-C. Desplat in *J. Stat. Phys.* (under review). A deep quench was chosen in which the fluid-fluid interface should be sharp on the scale of a colloid (see below) and the thermal excitations of the interface (thermal capillary waves) are negligible. Thermal noise is however fully included in the description of fluid momentum—this imparts Brownian motion to the colloids. Physically relevant control parameters are then the viscosity $\eta$, the particle radius a, the fluid-fluid interfacial tension $\sigma$ and the thermal energy $k_BT$. (The fluid density $\rho$ can be scaled out.)

For the binary fluid system the lattice Boltzmann method was used, incorporating spherical solid particles. The code currently runs under open-MP on shared memory parallel machines, while an MPI (Message Passing Interface) version is currently under development for use on larger, distributed memory machines. For the binary fluid alone, spinodal decomposition has been extensively studied with this code and the methodology is well validated in that context. For colloids a standard 'bounce-back on links' method was used, modified to allow for the binary solvent. Brownian motion is achieved by a fluctuating fluid method distinct from, but closely related to, that of Ladd in *J. Fluid Mech.*, 271, 285 (1994); *J. Fluid Mech.* 271, 311 (1994).

The characteristic length and time scales associated with the physics of coarsening are $L_0=\eta^2/(\rho\sigma)$ and $t_0=\eta^3/(\rho\sigma^2)$ which for the physical parameters chosen in the main text are $L_0 \approx 14$ nm and $t_0=0.22$ ns. Computing the same quantities in the 'lattice units' of LB allows length and time scales to be matched to experiment, in principle. However, not all the dimensionless control parameters can fully be matched in practice. For example the Reynolds number, $Re=(dL/dt)\rho a/\eta$ which characterises the relative importance of fluid inertia to viscosity, can be made small compared to unity, but not as small as the physical value. $\epsilon/k_BT$ and $a/L_0$ are fully matched as described previously. The identification of the longest runs as 300 ns in duration then follows from the definition of $t_0$. To faithfully represent fluid-fluid-solid wetting behavior it is also required that $1\ll\xi\ll a$ in lattice units; but this is only marginally achievable (see below for values).

Two simulations were performed using a lattice of $128\times 128\times 128$ sites with periodic boundary conditions. The main production runs took around 1 week on a 32-processor IBM p690+ system and some 2-3 weeks on a 48-processor Sun E15K system. These were accompanied by further runs at the same scale, and many smaller $64^3$ and $32^3$ runs, to check that physical trends were as expected. If the system is too small, fluid motion will be artificially arrested once L approaches the box size (with the interface then attaining state of zero mean curvature in three dimensions) even in the absence of a monolayer of particles. This state was often reached with the smaller system sizes. However, FIG. 7, which shows the domain length scale as a function of time, confirms that in the $128^3$ runs, L remains significantly less than the system size: the drastic slowdown of coarsening is not a finite-size effect. The free energy parameters were A=-0.002, B=0.002, and $\kappa$=0.0014 giving an interfacial thickness of $\xi$=1.14, tension $\sigma$=0.0016, fluid density $\rho$=1, and viscosity $\eta$=0.1 (all in lattice units). The fluid was initialized to be well mixed and at rest. A small amplitude random noise was added to the $\Psi$ field to induce spinodal decomposition. At the same time, colloids were positioned at rest randomly throughout the system. Thermal fluctuations appropriate to a temperature of 300 K were included. The first simulation is a monodisperse suspension with 8229 particles of radius a=2.3 lattice units (corresponding to 5.4 nm in physical units) providing a solid volume fraction of 20%. The bidisperse simulation has 4114 colloids of radius a=2.3 and 2407 larger particles of radius a=2.7 lattice units. Both simulations were run initially for 520,000 time steps, which is 275 ns in physical time; the bidisperse run was then run on further, to examine cross-flow (see below).

Note that longer physical time scales (of order milliseconds) would be achieved if parameters to model micron-scale colloids rather than nanocolloids were chosen. However, it is currently not practicable to run for timescales very long compared to the Brownian relaxation time of a free colloid (of any size) while still maintaining realistic values for $L_0$ and $t_0$ as required for the coarsening problem.

On the lattice the colloids are discrete, block-like, objects. To take account of this, a calibration is performed to compute an appropriate hydrodynamic radius $a_h$. This is the radius of the sphere which exhibits the same mean Stokes drag factor $6\pi\eta a_h$ as the discrete colloid on the lattice. For the viscosity used here ($\eta$=0.1), the actual and hydrodynamic radius for the smaller colloids are found to be the same, $a=a_h=2.3$, while for the larger particles the hydrodynamic radius is slightly larger (a=2.74 and $a_h$=2.75). Fluid-mediated interactions between the particles are well represented within LB when colloids are separated on the lattice, but this breaks down when the colloid-colloid separation h drops below the lattice scale. This can be rectified by a standard procedure in which lubrication forces are added by hand. In these runs, the normal ($h^{-1}$) component of the pairwise lubrication interaction is corrected at interparticle separations h<h*=0.7 lattice units. A much weaker transverse component of the lubrication force is neglected.

The computation of the lubrication forces itself becomes a major numerical exercise, with bad ($N^3$) scaling in the number N of colloidal particles in simultaneous mutual lubrication contact. Since sequestration at the fluid-fluid interface results in very large N, a workround for this is essential. It is achieved by adding an additional pairwise thermodynamic potential ($\propto h^{-2}$) which effectively prevents particles approaching closer than roughly 0.3 lattice unit. This results in a visible residual spacing between particles in the interfacial monolayer. Such short range repulsions are quite common physically and do not seriously compromise the realism of our simulations.

In contrast to this treatment of the lubrication forces, no equivalent corrections to the interparticle forces take place in the thermodynamic sector. Thus, for a dense particle layer, there may be relatively few fluid-fluid nodes left in the interstices. This underestimates interfacial energies, and could account for continued slow coarsening and detachment after particles become densely packed on the interface. In particular, a narrow neck, only one or two particles across, could become internally 'dry' with no fluid nodes containing the enclosed solvent. This problem is alleviated for the higher resolution runs for structural motifs; these have somewhat larger particle size but considerably larger length-scales for the interfacial structures (necks, bumps) themselves.

For the cross-flow simulation, a $\Psi$-dependent body force was applied to the fluid which drives the different phases in opposite directions. A pumped flow (driven by pressure gradients) is not expected to differ significantly. The body force was switched on after near-arrest was complete at 520 K time steps and the simulation run on to 600 K steps to allow a near-steady flow to establish. The mean of the velocity was recorded over the final 20K steps and used to generate the streamline ribbons. A small number of free particles (not attached to the interface) move discernibly during this time; the interfacial motion itself is negligible. In a separate run, the forcing was increased to test the resilience of the structure. A transient (~0.5 ns) forcing twenty times stronger than the previously described example led to significant distortion of the interfacial structure followed by partial elastic recovery when forcing was removed. However, it was apparent that this forcing, if maintained, would lead to structural meltdown.

To check the role of Brownian motion, this was switched off midway through a run whose initial parameters were that as described earlier. There was a reduction in visible wobbling of particles at the interface, but little effect on the macroscopic motion. Reducing the thermal noise level is equivalent to increasing the particle radius; even with no noise from the outset of the run, very similar results to those presented above were found. It can be concluded that the physics of arrest is largely independent of Brownian motion and hence of particle size. Similar checks were made for the role of attractive bonding interactions between colloids. It is possible that very strong attractions (as might be required to compete effectively with interfacial forces) could have a strong effect, but for bonding energies of up to several times $k_B T$ no discernible difference from the purely repulsive runs described above were found.

The higher-resolution studies were done using the same fluid parameters as before, but with somewhat larger average particle sizes (2.7 and 4.1 lattice units for the cylinder, 2.1 and 3.2 for the rippled surface). These particle sizes correspond to physical radii of 5 nm to 9 nm for the model aqueous/hydrocarbon mixture ($\eta=10^{-3}$ Pa s, $\rho=10^3$ kg m$^{-3}$ and $\sigma=6\times10^{-2}$ N m$^{-2}$ at 300 K). For these studies, the thermodynamic interaction potential used to maintain a nonzero surface-to-surface contact distance h in the packed film comprised a screened Coulomb interaction with Debye length $\lambda=0.2$ lattice units, truncated with offset so as to vanish at and beyond h=0.4 lattice units. The amplitude of the interaction force (effectively, the surface charge) is chosen to engineer an equilibrium value of h=1.0 lattice unit for a regular triangular lattice of particles of the harmonic mean size as estimated by minimizing the total energy of a unit cell of this lattice. This maintains surface-to-surface spacing of particles in a dense layer at of order one lattice spacing, which, for the chosen particle sizes, ensures that the thermodynamics of the fluid-fluid interface in the interstices between particles is adequately resolved by the discretization.

ADVANTAGES AND OVERVIEW

Fluid-bicontinuous particle-stabilised gels represent a new genre of materials that can be tuned to demonstrate macroscopic rigidity or macroscopic fluidity over a range of temperatures and in a variety of conditions. They are robust against attack by external solvents and when macroscopically rigid, they retain their macroscopic rigidity indefinitely, even under external forces. Furthermore, fluid-bicontinuous particle-stabilised gels are extremely versatile, highly tunable and can exhibit further macroscopic properties such as photonic properties, high thermal conductivity, large interfacial area and adjustable pore size.

Fluid-bicontinuous particle-stabilised gels have some remarkable properties, many of which stem directly from the non-equilibrium, arrested nature of the materials, and that differ strongly from an otherwise analagous equilibrium phase: the bicontinuous microemulsion. (This is a broadly similar structure, but stabilised by an equilibrium fluid monolayer of surfactant rather than an arrested monolayer of colloids.) As already discussed, fluid-bicontinuous particle-stabilised gels are highly tunable in elasticity and pore size through the volume fraction and radius of the solid particles; the radius can be varied from microns to nanometers without impeding the physics of structure formation by the route reported here.

The present invention differs from previous work in which colloidal particles have been used to stabilize spherical emulsion droplets of one liquid in another. Under compression, such emulsions can form robust gel phases with interesting mechanical properties, but fluid bicontinuity is not among them. The currently preferred route to particle-stabilised emulsions involves agitation of immiscible fluids and does not appear to favour bicontinuity. Other related prior art involves particles with a strong preference for one of the two liquids, creating a particle network within the chosen liquid rather than at the interface.

Fluid-bicontinuous particle-stabilised gels can be formulated so that they are permanently macroscopically rigid or, so that they are reversibly fluidisable. The first case arises when bonding interactions are present between the particles on the fluid-fluid interface. The second arises when the particles repel each other; the interface is then rigid because the particles are jammed together but can be mobilized by expanding the interfacial area.

In fluid-bicontinuous particle-stabilised gels, the fluids are arranged in such a way that they both span the entire sample and have a huge mutual interface; this interface is stabilized by colloidal particles alone. The two percolating liquid domains, the large interface and the promising visco-elastic properties make these structures attractive for various applications.

It should be noted that the fluid-bicontinuous particle-stabilised gels may have several applications in a variety of technologies, some of which have not been mentioned explicitly herein. In particular, fluid-bicontinuous particle-stabilised gels will be useful in the fields of personal care formulations, foodstuffs, drilling muds and pharmacology.

The arrangements shown in the Figures are exemplary only, and it will be apparent that other arrangements of the fluid-bicontinuous particle-stabilised gels can exist. For example, the fluid-bicontinuous or multicontinuous particle-stabilised gels can be formed using a plurality of immiscible fluids that form bicontinuous states when adjoined at an interface by means of any particle.

Further modifications and improvements may be incorporated without departing from the scope of the invention herein intended.

The invention claimed is:

1. A fluid-bicontinuous particle-stabilised gel comprising:
a first fluid and a second fluid which are immiscible within a specific temperature range; and
a stabilising particle layer comprising a continuous layer of stable particles in intimate contact, the particles positioned at a continuous interface between the first fluid and second fluid, wherein the first and second fluid are interpenetrating domains.

2. A fluid-bicontinuous particle-stabilised gel according to claim 1, wherein the first fluid is hydrophobic and the second fluid is hydrophilic.

3. A fluid-bicontinuous particle-stabilised gel according to claim 1, wherein one of the fluids is selected from the group consistoing of an oil, water and an alcohol.

4. A fluid-bicontinuous particle-stabilised gel according to claim 1, further comprising a strongly fluid asymmetric fluid-bicontinuous state.

5. A fluid-bicontinuous particle-stabilised gel according to claim 1, wherein the continuous layer of particles comprises partially wetting (PW) particles.

6. A fluid-bicontinuous particle-stabilised gel according to claim 5, wherein the PW particles are near-neutral wetting (NNW) particles.

7. A fluid-bicontinuous particle-stabilised gel according to claim 6, wherein the NNW particles have a contact angle between 70 and 110 degrees.

8. A fluid-bicontinuous particle-stabilised gel as claimed in claim 5, wherein the PW particles are in an arrested state.

9. A fluid-bicontinuous particle-stabilised gel as claimed in claim 5, wherein the PW particles are magnetically active.

10. A fluid-bicontinuous particle-stabilised gel as claimed in claim 9, wherein the magnetically active PW particles are superparamagnetic.

11. A fluid-bicontinuous particle-stabilised gel as claimed in claim 5, wherein the PW particles are electrically conductive.

12. A fluid-bicontinuous particle-stabilised gel as claimed in claim 5, wherein the PW particles are selected from the group consisting of: silica beads; Janus beads; globular biomolecules; colloidal particles with mixed polymer surfaces comprising flexible chains of two types, A and B, spread across the PW particle surface, wherein A and B are chosen so that A has an affinity for the first fluid, and B has an affinity for the second fluid, or vice versa; spherical micelles, comprising an equal mixture of XZ and YZ block copolymers wherein X has an affinity for the first fluid, and Y has an affinity for the second fluid, or vice versa, and with Z insoluble in both the first and the second fluids; and colloidal particles with micro-heterogeneous wetting properties at different patches on respective surfaces.

13. A fluid-bicontinuous particle-stabilised gel according to claim 1, wherein the structure of the fluid-bicontinuous particle-stabilised gel comprises a fully ordered, three-dimensional periodic domain.

14. A fluid-bicontinuous particle-stabilised gel according to claim 1, wherein the structure of the fluid-bicontinuous particle-stabilised gel comprises an amorphous arrangement of two interpenetrating domains.

15. A fluid-bicontinuous particle-stabilised gel according to claim 1, wherein further particles, structurants or additives are present in one or both of the first and second fluids.

16. A fluid-bicontinuous particle-stabilised gel according to claim 1, further comprising particles with attractive interactions.

17. A fluid-bicontinuous particle-stabilised gel according to claim 1, wherein the particles are in a fluid or aggregated state, within one or both of the first and second fluids.

18. A fluid-bicontinuous particle-stabilised gel according to claim 1, further comprising emulsion droplets, in a fluid or aggregated state, within one or both of the first and second fluids.

19. A fluid-bicontinuous particle-stabilised gel according to claim 1, wherein the fluid-bicontinuous particle-stabilised gel comprises a plurality of interpenetrating domains, which comprise a multicontinuous fluid or gel structure, the fluid-bicontinuous particle-stabilised gel being simultaneously permeable to a plurality of mutually immiscible fluids.

20. A fluid-bicontinuous particle-stabilised gel according to claim 1, wherein the fluid-bicontinuous particle-stabilised gel is insoluble in water and oil based solvents but remains permeable to both oil and water based solvents.

21. A fluid-bicontinuous particle-stabilised gel according to claim 1, wherein the first fluid and the second fluid are of different refractive index, wherein the first fluid has a refractive index lower than the second fluid, or vice versa.

22. A fluid-bicontinuous particle-stabilised gel according to claim 1, wherein the fluid-bicontinuous particle-stabilised gel displays thermal conductivity, adjustable by formulation.

23. A fluid-bicontinuous particle-stabilised gel according to claim 1, wherein the fluid-bicontinuous particle-stabilised gel is adapted to transform to a substantially fluidised state.

24. A fluid-bicontinuous particle-stabilised gel as claimed in claim 23, wherein the fluidization is reversible.

25. A fluid-bicontinuous particle-stabilised gel as claimed in claim 24, wherein the fluid-bicontinuous particle-stabilised gel in the reversibly fluidisable state comprises an initial arrested state and a final re-arrested state that the fluid-bicontinuous particle-stabilised gel reverts to.

26. A fluid-bicontinuous particle-stabilised gel as claimed in claim 24, wherein the fluid-bicontinuous particle-stabilised gel in the reversibly fluidisable state is macroscopically pliable.

27. A fluid-bicontinuous particle-stabilised gel as claimed in claim 24, wherein the fluid-bicontinuous particle-stabilised gel in the reversibly fluidisable state comprises an initial arrested state, and a final re-arrested state, that have different morphologies.

28. A fluid-bicontinuous particle-stabilised gel as claimed in claim 27, wherein the re-arrested state comprises droplets, parallel flat layers or cylinders, whose properties on re-arrest are different from the initial arrested state.

29. A method of altering properties of a fluid-bicontinuous particle-stabilised gel comprising the step of using magnetism to alter the properties, the fluid-bicontinuous particle-stabilised gel comprising: a first fluid and a second fluid which are immiscible within a specific temperature range; and a stabilising particle layer comprising a continuous layer of stable particles in intimate contact, the particles positioned at a continuous interface between the first fluid and second fluids and wherein the first and second fluid are interpenetrating domains.

30. A method of altering the properties of a fluid-bicontinuous particle-stabilised gel according to claim 29, further comprising the steps of:

subjecting the fluid-bicontinuous particle-stabilised gel to a magnetic field, and removing the particles from the interface using the magnetic field, wherein the initial fluid-bicontinuous particle-stabilised gel is subsequently rendered entirely fluid by removal of the particles from the interface.

31. A method of making a gel, the method comprising the steps of:

providing PW particles into approximately equal volumes of at least two fluids, at a temperature where the fluids are miscible; and changing the temperature to one at which the fluids are immiscible, to cause phase separation of the fluids, thereby forming a gel having interpenetrating fluid domains with the PW particles positioned at a continuous interface between the fluids.

32. A method of making a gel according to claim 31, wherein the phase separation is spinodal decomposition.

33. A method of making a fluid-bicontinuous particle-stabilised gel, comprising the steps of:

dispersing PW particles in a mixture of two solvents by means of mixing, thereby creating a bicontinuous state with more interfacial area than is required to accommodate all of the PW particles, and stopping the mixing so that the PW particles come into intimate contact on a continuous fluid-fluid interface, precipitating gel formation.

34. A method of making a Janus bead, comprising the steps of:

mixing together approximately equal quantities of spherical micelles comprising XZ and YZ block copolymers, wherein X, Y and Z are polymer chains, in a solution comprising approximately equal volumes of at least two fluids, at a temperature range where the two fluids become miscible, and under such conditions that mixed micelles form spontaneously;

subsequently altering the temperature to a temperature in the temperature range where the fluids are immiscible, causing spinodal decomposition to form a two-phase region, and thereby sequestering the block copolymers at an interface between the fluids;

maintaining a temperature such that the Z polymer chains remain above their glass transition temperature and the XZ and YZ block copolymers migrate to opposite sides of the micelle; and altering the temperature such that the Z polymer chains pass through their glass transition temperature and the segregated micelle block copolymers are made stable, thus creating particles with hemispheres of opposite wetting properties.

35. A method of making a Janus bead, comprising the steps of:

preparing a fluid-bicontinuous particle-stabilised gel; and coating substantially one half of the particles in the fluid-bicontinuous particle-stabilised gel with substances that are dissolved in one or both of the first fluids and the second fluids.

36. A generic method of making a gel, comprising the steps of:

dissolving NNW particles in a solution comprising approximately equal volumes of at least two solvents, immiscible at a defined temperature range, at a second temperature range where the two solvents become miscible; and changing the temperature to a two-phase region where the solvents are immiscible, causing phase separation, thereby sequestering the NNW particles at an interface between the solvents.

37. A generic method of making a fluid-bicontinuous particle-stabilised gel, comprising the steps of:

dispersing NNW particles in a mixture of two solvents by means of mixing, thereby creating a bicontinuous state with more interfacial area than is required to accommodate all of the NNW particles; and stopping the mixing so that the NNW particles come into intimate contact on a continuous fluid-fluid interface, precipitating gel formation.

* * * * *